US011847610B2

(12) United States Patent
Delaney et al.

(10) Patent No.: US 11,847,610 B2
(45) Date of Patent: *Dec. 19, 2023

(54) PRODUCT STORAGE AND RETRIEVAL

(71) Applicant: Maxor National Pharmacy Services, LLC, Amarillo, TN (US)

(72) Inventors: Kevin C Delaney, San Jose, CA (US); Kendrick S Lim, Dublin, CA (US); Robert G Guillermo, Milpitas, CA (US)

(73) Assignee: Maxor National Pharmacy Services, LLC, Amarillo, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/372,704

(22) Filed: Jul. 12, 2021

(65) Prior Publication Data
US 2021/0342773 A1 Nov. 4, 2021

Related U.S. Application Data

(60) Division of application No. 16/533,123, filed on Aug. 6, 2019, now Pat. No. 11,080,651, which is a continuation-in-part of application No. 15/453,145, filed on Mar. 8, 2017, now Pat. No. 10,373,114, which is a division of application No. 13/741,075, filed on Jan. 14, 2013, now Pat. No. 9,619,777, which is a continuation-in-part of application No. 13/712,814, filed on Dec. 12, 2012, now Pat. No. 8,700,204, which is a continuation of application No. 12/196,078, filed on Aug. 21, 2008, now Pat. No. 8,355,962.

(51) Int. Cl.
*G06Q 10/087* (2023.01)
*G06Q 50/22* (2018.01)

(52) U.S. Cl.
CPC .......... *G06Q 10/087* (2013.01); *G06Q 50/22* (2013.01)

(58) Field of Classification Search
CPC ....... G06Q 10/087; G06Q 50/22; G16H 20/10
USPC .......................................................... 705/28
See application file for complete search history.

(56) References Cited

U.S. PATENT DOCUMENTS

| 7,477,597 B2 * | 1/2009 | Segel ................. H04B 7/18591 370/230 |
| 7,685,026 B1 * | 3/2010 | McGrady ............... G06Q 10/08 705/28 |
| 2003/0052786 A1 * | 3/2003 | Dickinson .............. B65D 81/03 340/572.8 |
| 2003/0218537 A1 * | 11/2003 | Hoch ................... H05B 47/105 340/524 |

(Continued)

Primary Examiner — Garcia Ade
(74) Attorney, Agent, or Firm — Dergosits & Noah LLP

(57) ABSTRACT

A inventory system for product storage and retrieval. Ordered goods are placed in bag units at a central filling center and shipped to local storage areas, where the bags are placed onto rails in a storage structure. The rails include an imaging sensor at each bag receiving location defined on the rails for obtaining a bag identifier that is affixed with the bag unit. The bag identifier and the rail address for each bag unit is stored on a local computer database. When a user wants to pick up stored goods, the user inputs the identification or order information for the goods and the computer will search the inventory to locate the goods in a specific stored bag unit. The rail adjacent the bag unit is illuminated to facilitate locating the goods.

8 Claims, 25 Drawing Sheets

(56) References Cited

U.S. PATENT DOCUMENTS

2008/0191842 A1\* 8/2008 Spenik ................ G06K 7/0008
340/10.1

\* cited by examiner

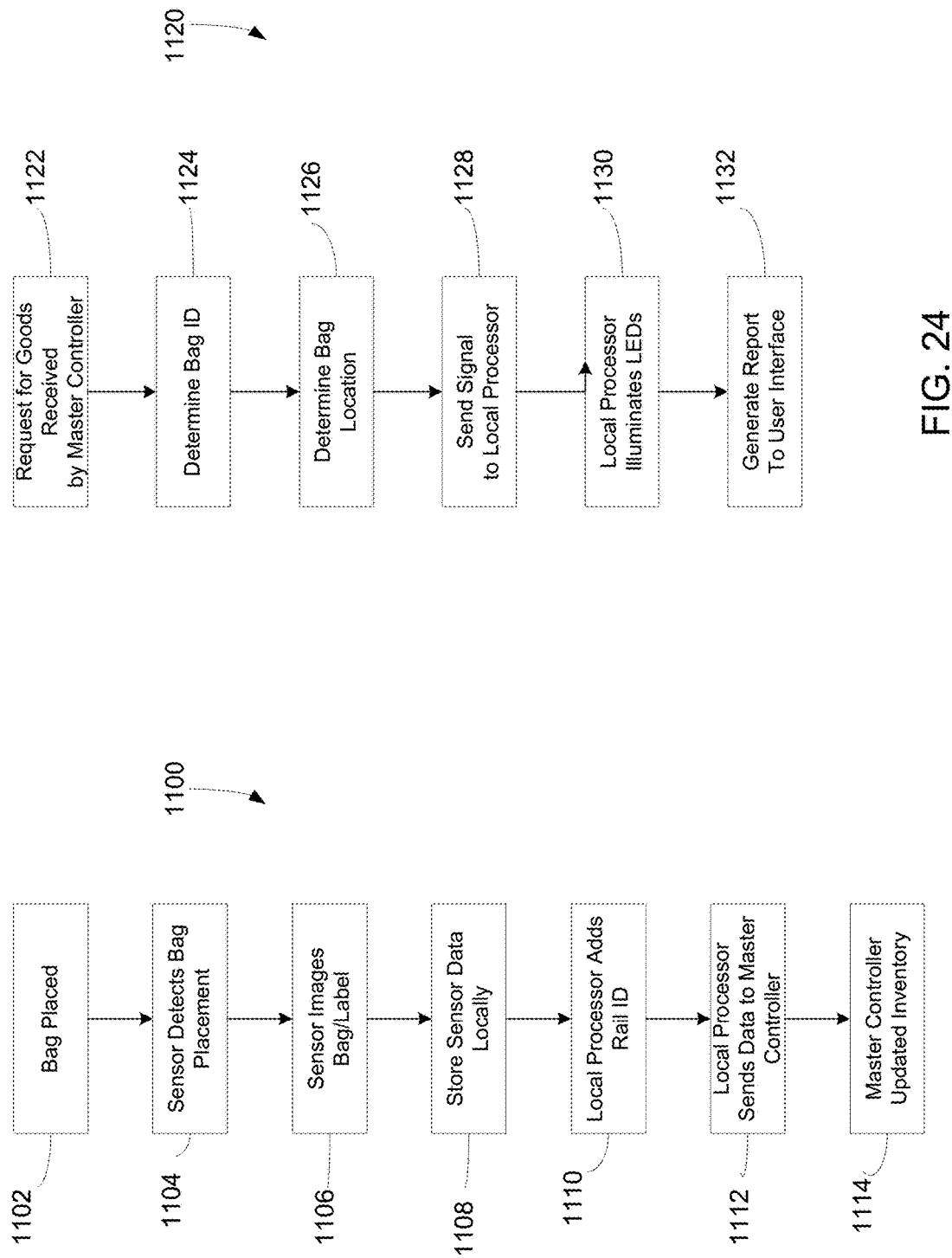

PRODUCT STORAGE AND RETRIEVAL

BACKGROUND

An inventory of goods is frequently stored in a storage area. The distribution of the goods is monitored and controlled by inventory workers. When an order is placed for the goods, a pick list is produced and the inventory workers obtain the required quantities of each of product on the pick list. The ordered goods can then be placed in a temporary storage area until the order is picked up. Because many orders can be placed at the same time, the filled orders must also be identified and organized so they can be easily located and given to the proper recipient. When the order is picked up, order information or identification information is given to the inventory workers who locate the filled order and gives the order to the recipient.

When the goods are controlled, it may be necessary to store the goods in a secure area. For example, a pharmacy may store many different drugs in an area that is only accessible to authorized employees such as pharmacists. A prescription from a doctor may be required to place and fill the order for these drugs. When an order is placed, a pharmacist will place the specified quantity of drugs into a container and then place the container in a storage area with the name of the patient marked on the container. When the patient picks up the prescription drugs, the pharmacist will compare the patient's identification with the patient's name on the prescription before delivering the medication(s) to the patient.

A problem with existing systems is that they are inefficient since the user must manually locate the products in the inventory area which are typically stored in a numeric or alphabetical order. There is also a problem of locating the filled orders that have been placed in the temporary storage area. Since these tasks are performed manually, the location of goods and filled orders can require sorting through many items before the correct goods and filled orders can be located. It can be very difficult to pick out goods and filled orders with 100% accuracy. What is needed is a system that allows users to more easily locate goods in an inventory storage area or find filled orders within a temporary storage area.

SUMMARY

This disclosure is directed towards modular hangers which are used for storing and locating goods in one or more local storage areas. The storage apparatus can include one or more rails that are used to support a plurality of modular hangers and provide electrical power to the modular hangers. Each modular hanger can have a hook unit and a storage unit. The hook unit can be coupled to the storage unit or separated from the storage unit. The modular hanger can also include a locking mechanism that prevents the accidental separation of the hook unit from the storage unit. The hook unit can include a microprocessor, an indicator light and a transceiver. The storage unit can include an electronic memory storing a unique hanger address and a bar code or other identification mechanism.

The modular configuration allows the storage units to be separated from the hook units which can be useful when the storage units are filled with goods at a remote location such as a central fill location and then transported to a local storage area. In an embodiment, customers can order goods which are recorded in a computer database. When the order is filled, the ordered goods can be placed in one of the storage units at the central fill location. During the order filling process, the ordered goods can be paired with the ID of the storage unit storing the ordered goods. The order ID and the storage unit ID information can also be stored in a database of a central computer. For example, the bar codes of the filled storage units can be scanned to record the ID information.

The filled storage units can then be placed in shipping containers that are shipped to local distribution centers. ID information for the shipping containers can also be scanned and stored in the central computer. At the local distribution centers, the storage units can be removed from the shipping containers and the storage units can be scanned and stored in the local distribution center computer. The storage units can then be coupled to hook units to form assembled modular hangers. These modular hangers can then be placed on storage rails at the local distribution centers. When the modular hanger is placed on the storage rail, electrical power from the storage rail can supply electrical power to the modular hanger and cause the modular hanger to emit the hanger address as a radio frequency signal to the local distribution center computer. The receipt of the ID signal can confirm that the ordered goods have been stored on the storage rails and are ready for pick up.

After the order is confirmed to be in the local storage area, the system or a worker may inform the customer that the order is ready for pick up and the customer may come to the local distribution center to pick up the order. When the customer arrives and requests the order, an operator can input the goods or order information into the local computer and the corresponding hanger address can be obtained. The local computer can then transmit the hanger address in a signal to the modular hangers and the hanger having the matching address can illuminate its light. The operator can then easily locate and remove the modular hanger from the rail and remove the goods from the storage unit. The goods and ID information can again be recorded to the computer to confirm the delivery of the order to the customer. After the order transaction is complete, the hook unit can be removed from the storage unit and the storage unit can be returned to the central filling center and the hanger unit can be reused at the local distribution center. The described process can be repeated.

The ability to separate the hanger portion from the storage portion can be beneficial in a large "central fill" system which distributes goods to many local distribution centers. In these embodiments, a central filling center can store various goods and have a supply of storage units. Orders may be received and processed by the central filling center. The orders can be placed in storage units and the addresses for each order can be recorded on a central fill computer database. The ordered goods in the storage units can then be placed in shipping containers which are shipped from the central filling center to each of the local distribution centers. An electronic record of the goods and corresponding hanger addresses can also be transmitted to the local distribution center computers to allow the receipt of the orders to be confirmed. The storage units are also checked when they are received at the local distribution centers and when they are placed in storage. By monitoring the storage units throughout the delivery and receiving processes, the status of the goods can always be determined by the central filling center computer and the local distribution center computers.

In an embodiment, the efficiency of the inventive system can be enhanced by placing multiple goods ordered by the same customer in the same storage unit during the order filling process. The storage units can then be placed in shipping containers with other storage units ordered by different people but going to the same local distribution center placed in the same shipping containers. The shipping containers can be received by the local distribution centers and each of the storage units containing multiple goods can be connected to a hook unit to form modular hangers. Each modular hanger can be placed on a storage rail which can provide electrical power to the modular hanger and emit the address signals as described above.

The inventive system can also be used to detect errors. When the shipping containers are received by the local distribution centers, the shipping container identification codes can be scanned and input into the local distribution computers. The scanned identifications can be compared to the expected shipping container identifications. The shipping container identifications can be transmitted from the local distribution center server to the central fill server to either confirm receipt or identify a delivery error. If a delivery error has been made, the central fill server can instruct the local distribution center to ship the shipping container back to the central fill center or to the proper local distribution center.

As the storage containers are removed from the shipping containers, the bar codes can be scanned and the local distribution server computer can compare the scanned storage containers to the listing of expected storage containers. If there are discrepancies, the local distribution computer can inform the central fill computer that there are improperly shipped or missing storage containers. The local distribution server can also initiate procedures for a local search for any missing storage containers and return any improperly shipped storage containers to the proper local distribution center.

When a user requests the goods associated with the hanger ID, the computer transmits a data packet that includes the hanger ID to the storage area. The modular hangers receive the data packet and the modular hanger that has the matching hanger ID illuminates an indicator light so that a user can quickly determine the hanger which is storing the requested goods. A user can remove the modular hanger from the rail and provide the goods to the purchaser to complete the order transaction. After the goods have been removed from the modular hanger, the locking mechanism can be released so the hook and storage units can be separated. The storage units can be placed back in the shipping containers and sent back to the central filling area for reuse. The hook units can remain at the local distribution center be attached to new storage units received by the local distribution center. The storage units or hook units can be replaced as necessary.

In an embodiment, the light on each of the modular hangers can include one or more light emitting diodes which can each be different colors, such as red, green and blue. By simultaneously illuminating a combination of these lights at different intensities, the combination of these lights can produce various different colors. In the preferred embodiment, the inventive system is coupled to a computer network that includes a plurality of computers and the inventive system can be controlled by one or more In an embodiment, many different products or orders may be retrieved simultaneously and several different modular hangers can be illuminated simultaneously. In order to distinguish the illuminated hangers associated with each of the different products or orders, each of the hangers can be illuminated in a different color and/or flash pattern. When the computer transmits a packet with a hanger address, additional illumination instructions can also be included in the packet. The light instructions can specify an illumination color and a flash pattern. When the hangers receive the data packets that include address signals and illumination instructions, they will first determine if the address in the data packets matches the received address and if the addresses match. If there is a match, the hanger will read the illumination instructions. The illumination instructions can instruct the hangers to illuminate the indicator lights in distinct colors or blinking patterns. For example, two addresses may be transmitted from the client computer to the modular hangers. A first hanger can be a match for the first address and the corresponding illumination instructions may be a fast pulsing red light. A second hanger can be a match for the second address and the corresponding illumination instructions can be a slow pulsing green light so that the worker can distinguish the first and second orders.

The local computer will provide a description of the illumination associated with each of the goods or orders so a user or worker can find the matched hangers based upon the illuminated light display. When the modular hangers are found and removed from the rail, the light may no longer be illuminated. The user can check the delivery of the goods to the customer by scanning the storage unit ID and record this information to the computer. The computer may also record the receipt of goods by the recipient using an input device such as: a signature, a credit card, a biometric finger print reader, driver's license magnetic strip or any other type of identification mechanism. In other embodiments, the hanger illumination colors and flash rates can be designated by workstation, by user, or any other identifiable feature. This can allow a specific worker to select a single flash pattern to search for with each worker having a dedicated flash pattern.

In an embodiment, an additional check can be performed to insure that the proper goods are being delivered to the recipient. The hangers may have a secondary identification device such as a bar code, serial number code, radio frequency identification tag, magnetic coding, etc. The secondary code associated with the hanger can be read by a corresponding input device to verify that the secondary code matches the order. These secondary identifications can be associated with the goods or filled orders prior to storing the hangers on the rails. When the storage units is retrieved from the storage area, the address of the hanger can be compared to the goods and the secondary identification can also be checked. A mismatch between the secondary identification can indicate an error in the goods or order.

Although most goods will be delivered to customers, some of the goods may be returned, may expire prior to pick up or never picked up. In all of these situations, the goods can be returned to the central fill location. When the goods are returned to the central fill location, the returned goods can be processed in an appropriate manner. For example, the expired goods can be destroyed, the returned goods and goods that were never picked up can be restocked and the goods delivered to the wrong distribution center can be shipped to the proper local distribution center.

The inventive system can also be used to help location lost or missing storage units that have been improperly shipped to the wrong local distribution center. Identification information for the lost storage units can be sent to the central server and transmitted to each of the local distribution centers. The addresses for each of the lost or missing storage units can be transmitted at each local distribution center and if a storage unit responds to the address signal, the storage unit can be retrieved and returned to the central distribution center or shipped directly to the proper local distribution center.

BRIEF DESCRIPTION OF THE DRAWINGS

FIG. 23 is a flow chart illustrating a process for bag placement and detection.

FIG. 24 is a flow chart illustrating a process for locating a bag that has been placed.

DETAILED DESCRIPTION

The present invention is directed towards an apparatus and system for storing and locating products that includes modular hangers that have a storage unit and a hook unit. In one embodiment, a simple bag unit is placed onto a rail, and the rail detects the placement and updates inventory.

Figure 1:
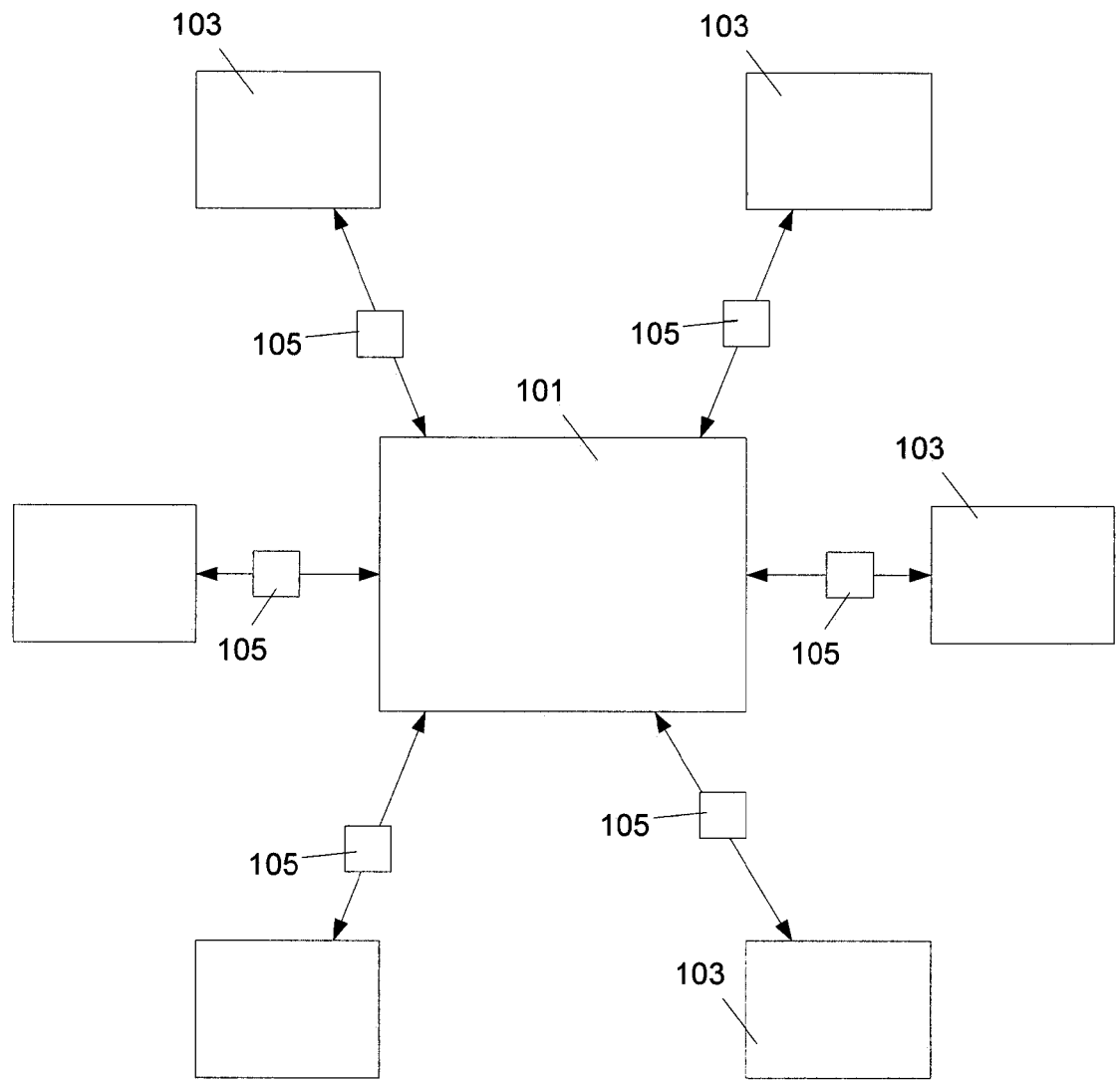
FIG. 1 is a block diagram of an embodiment of the distribution system.

With reference to FIG. 1, orders can be filled in a central filling center 101 and transmitted to local distribution centers 103 for distributing goods to customers. The ordered products can be placed into storage units at the central filling center 101 and the hanger address for the storage unit and a description or identification code for the products in the storage unit can be recorded through a central computer and stored on a database. Each order can be placed in one or more storage units. The filled storage units can then be placed in shipping containers 105 and shipped from the central fill center 101 to various local distribution centers 103. Multiple different ordered products going to the same local distribution centers 103 can be placed into the same shipping containers 105. Listings of goods for each shipping container 105 can also be created and transmitted from the central computer at the central filling center 101 to local computers at each of the local distribution centers 103 electronically through a communications network connection. The listing of goods can include the hanger address for the storage unit and a description or identification code for the products in the storage unit.

When the shipping containers 105 are received at the local distribution centers 103, an identification barcode for the shipping container 105 can be scanned and the bar codes for each storage unit can be scanned. The local computer can compare the inventory listing of goods sent electronically to the storage units actually received. The system can identify any missing storage units or extra storage units that were received by accident. The scanned storage units are coupled to hook units to form modular hangers which are placed on rails in the local distribution centers 103. The modular hangers can receive electrical power from the rails and use the electrical power to transmit their hanger addresses or IDs to the local computers and the system can confirm that the ordered products in the storage units are ready for pick up at the local distribution centers 103. The local computers or a worker may then inform the customers that their ordered products are ready for pick up. When the customer goes to the local distribution center 103, the order information is provided and the local computer transmits the hanger address for the modular hanger coupled to the ordered goods. The modular hanger is retrieved and the goods are given to the customer. The empty storage units can be separated from the hook units and placed back in the shipping containers 105 for shipment back to the central filling center 101 and the hook units can be coupled remain at the local distribution centers 103 and coupled to other filled storage units.

Figure 2:
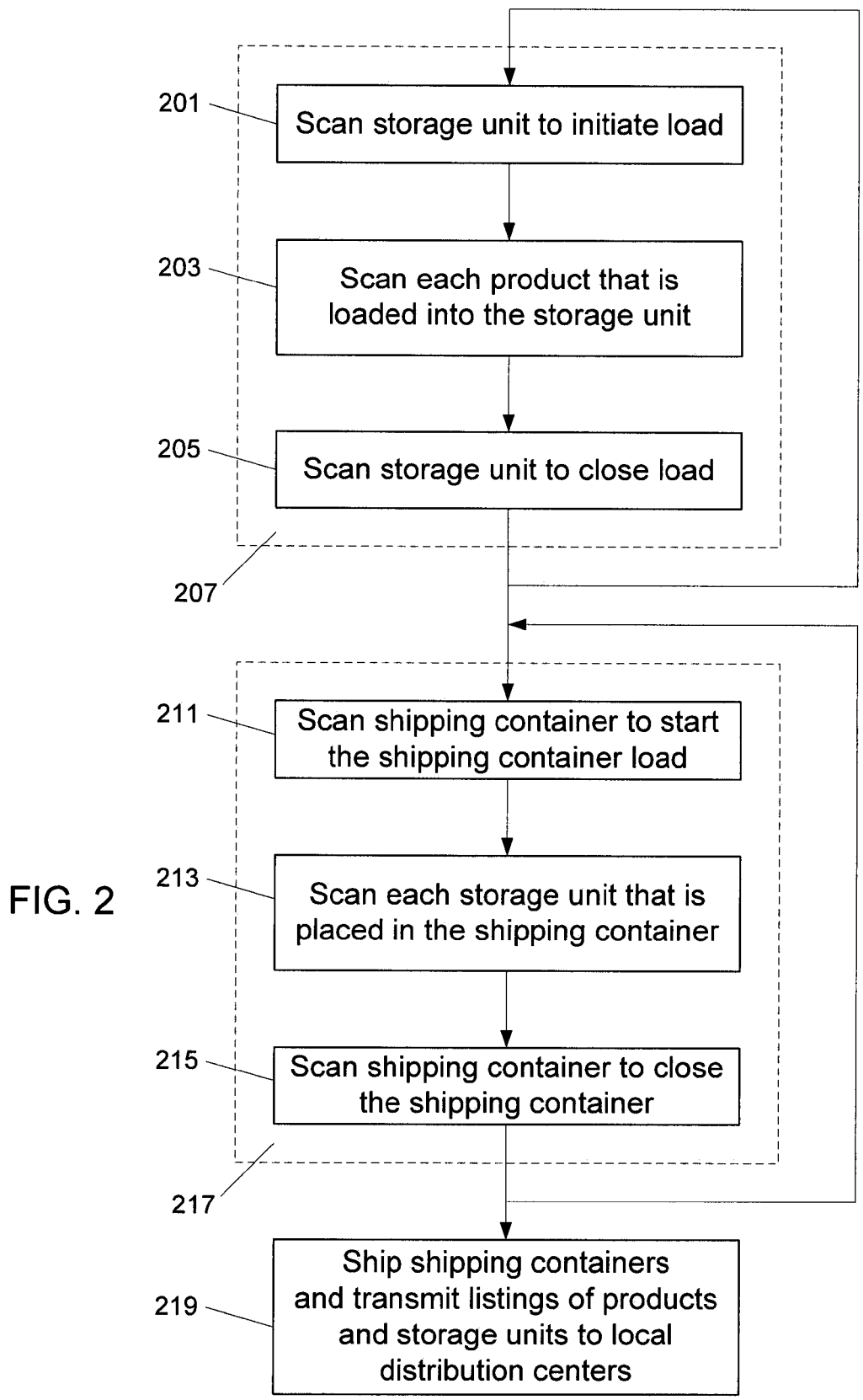
FIG. 2 is a flow chart for loading products into storage units into shipping containers and shipping the shipping containers to local distribution centers.

Specific procedures can be performed to perform the product distribution method. With reference to FIG. 2, a flow chart of an exemplary order filling process 207 and shipping container filling process 217 are illustrated. The storage unit can include a unique bar code and hanger address that is stored in an electronic memory within the storage unit. The storage unit can be scanned to initiate the load 201. The ordered goods are then scanned in a similar manner with a bar code reader before placing the goods into the storage unit 203. The storage unit 203 can be scanned again to finish the load 205. The goods information and storage unit information can be recorded and stored together in a database of the central computer. The storage unit filling process 207 can then be repeated until all ordered goods are placed in storage units 203 and all goods and storage unit information is recorded.

The filled storage units can then be placed into shipping containers with an exemplary filling process 217. The shipping container code can be scanned to start the shipping container load 211. An identification barcode or tag for each storage unit can be scanned before placing the storage units into the shipping container 213. The shipping container code can be scanned a second time to finish the shipping container filling process 215. The shipping container filling process 217 can then be repeated for the next shipping container until all filled storage units have been placed into one of the shipping containers. Each shipping container can be delivered to a specific local distribution center so only storage units going to the same local distribution center may be placed in the same shipping container. In an embodiment, the scanning of the codes on the storage units, products and shipping containers can be performed with a bar code scanner. However, in other embodiments, the scanning can be performed by any other suitable means including RFID readers, transceivers coupled to the storage unit electronic memory, memory device readers, etc.

Although, the order filling 207 and shipping container filling processes 217 are described as two distinct processes, in other embodiments, the order filling 207 and shipping container filling 217 can be performed together. For example, immediately after the order filling 207 for each storage unit is complete, each filled storage unit can be automatically placed in a shipping container. In an embodiment, one or more machines can be used to automatically scan and pack each of the shipping containers with filled storage units.

Figure 3:
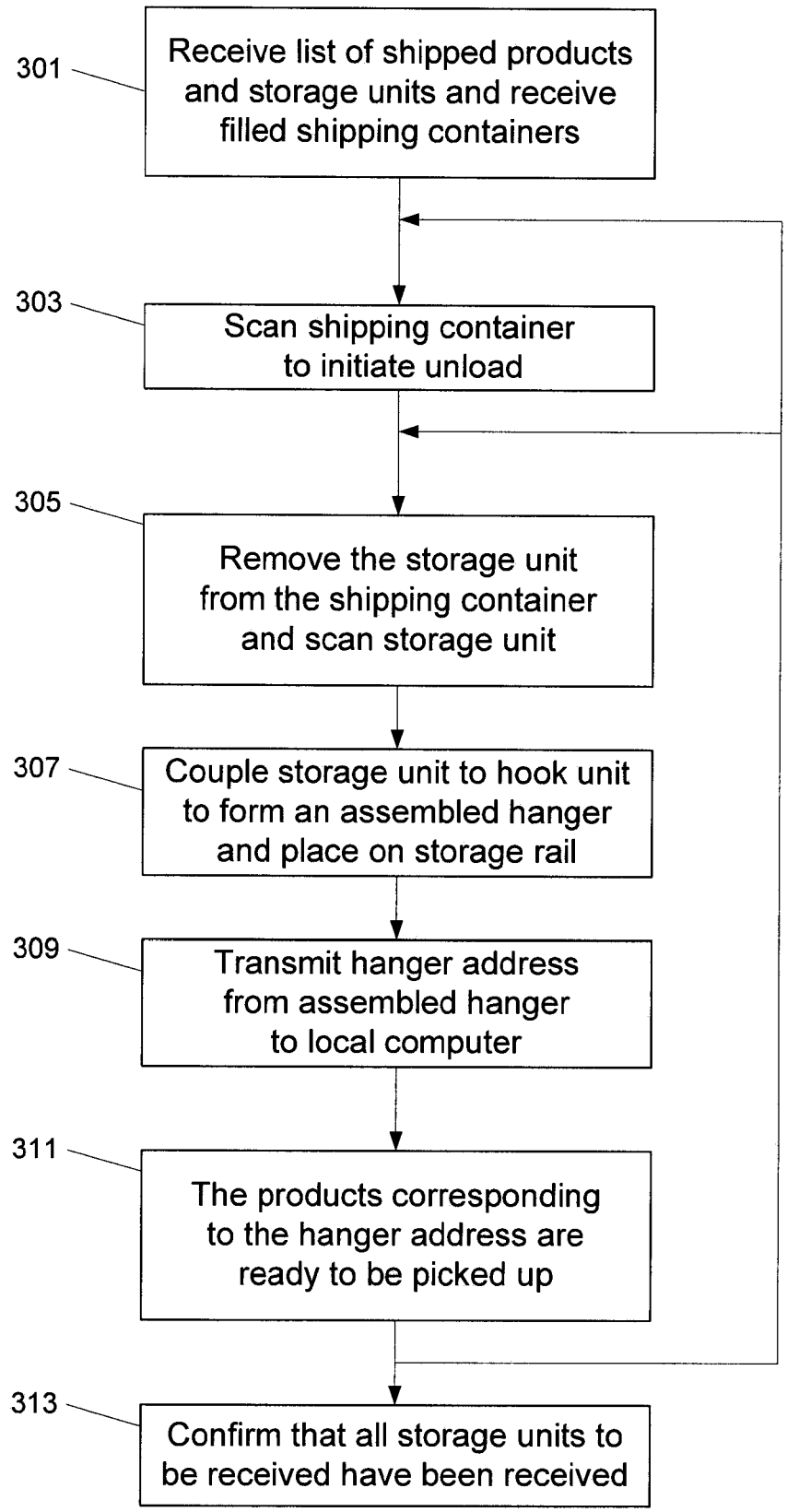
FIG. 3 is a flow chart for unloading storage units from the totes and placing assembled modular hangers on storage rails at the local distribution centers.

With reference to FIG. 3, a flow chart for an exemplary shipping container receiving process is illustrated. Listing of goods and storage units can also be created and transmitted by the central computer and received by local computers at each of the local distribution centers for each shipped shipping container. These listings can be transmitted electronically through a network, cellular network, the Internet or any other suitable means and stored as a listing of goods to be received on a local database 301. When the shipping container is received by the local distribution centers, the shipping container code can be scanned to initiate the unload 303. The shipping containers can then be opened and the storage units can be removed. Each storage unit can then be scanned and the scanned storage unit data can be stored in the local computers at each of the local distribution centers 305. The local computer can receive the storage unit identifications and remove the products associated with the age units from the listing of products to be received. The storage units can each be coupled to a hook unit to form an assembled modular hanger and the assembled modular hangers can be placed on a storage rail 307. As discussed, the storage unit can include a hanger address stored in an electronic memory. The hook unit can include other electronic components including a microprocessor, a radio frequency (RF) transceiver and electrical power contacts. When the storage unit is coupled to the hook unit, the electronic memory can be electrically coupled to the microprocessor and RF transceiver. In other embodiments, other types of wireless communications can be used between the system components. For example, optical transceivers such as infrared spectrum or sonic transceivers can be used for system communications instead of RF transceivers.

The storage rail may provide electrical power to the microprocessor and RF transceiver so that these electronic components may be functional. In response to the initial power input, the microprocessor may cause the RF transceiver to transmit the hanger address as a radio frequency signal to the local computer 309. The local computer can receive the hanger address signal and place the products associated with the hanger address on a listing of products that are ready to be picked up 311. This process can be repeated until all of the storage units have been removed from the shipping containers. The system may also confirm that all products and storage units on the listing of goods to be received have been received 313. With the modular hangers on the storage rails, the local storage area is ready for customers to pick up their ordered products.

If any errors are detected, the local computer can alert an operator that an error has been detected. Errors may include missing products or hanger addresses on the listing of products to be received as well as products or hanger addresses that have been received but are not on the listing of products to be received. Once the error has been identified, the central filling system may require the local storage area to ship a storage unit to another local storage area or back to the central filling area.

Figure 4:
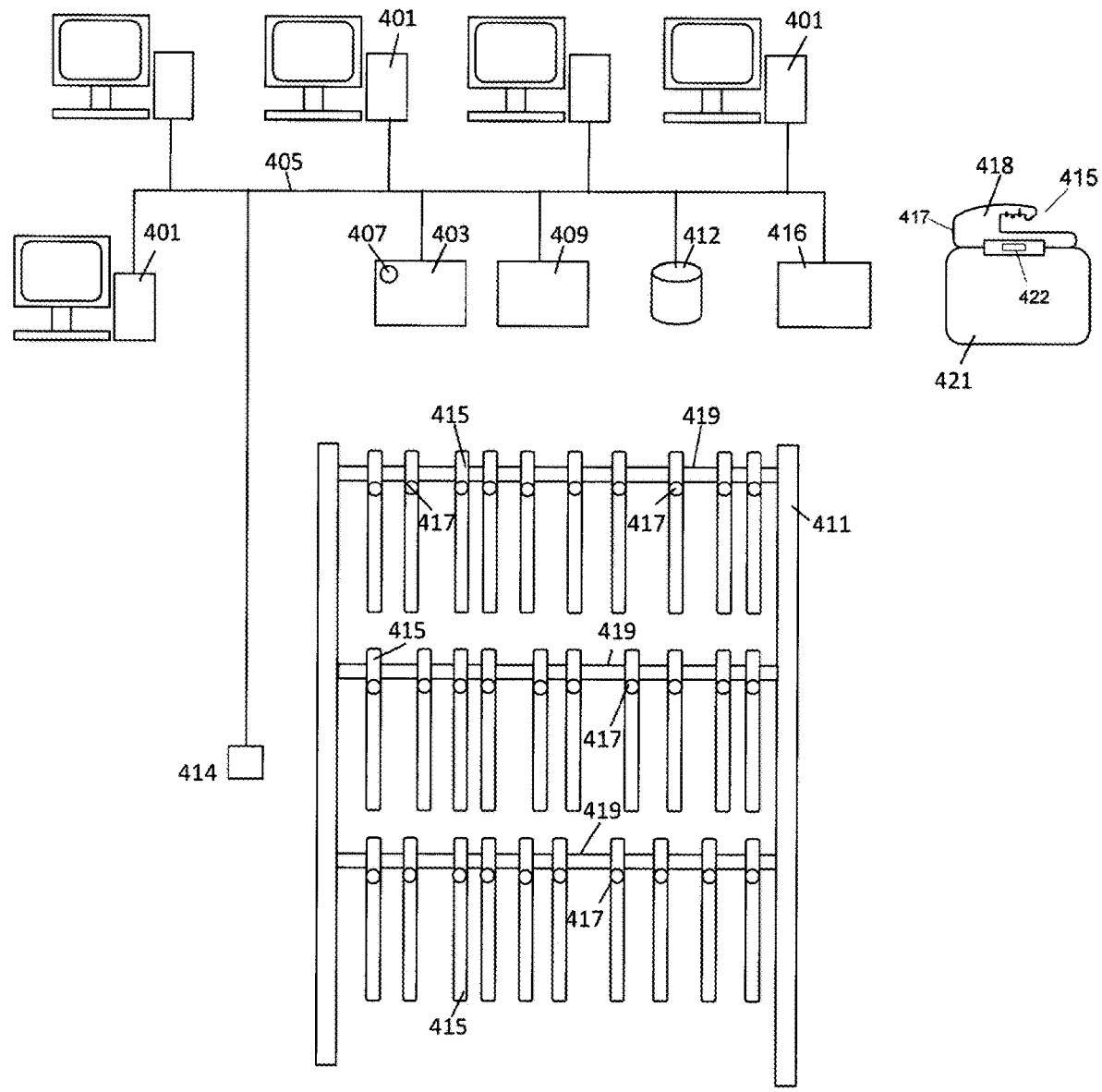
FIG. 4 is a diagram of the components at the local distribution centers.

With reference to FIG. 4, in an embodiment the local distribution centers can include several separate components. The inventive system can be used with a computer network having a plurality of client computers 401. The client computers 401 are coupled to one or more radio frequency (RF) transceivers 403. One or more of the client computers 401 can be an administrative computer that controls the operation of the inventive system.

The goods and the addresses of the hangers are associated with each other and this association is stored on a database 412 that is accessible by the client computers 401. The system may include an input device 418 which can be used to read information such as RFID tags or bar codes attached to the hangers. For example, goods that have a UPC code will also have a bar code and the scanner 418 can be a bar code reader. An operator of the system can scan the bar code with the input device 418 that communicates with the computer 401 through a wired or a wireless connection. Other possible input devices 418 can include optical scanners, RFID tag readers, magnetic strip readers and other data input devices. By scanning or reading an address for the hangers and an identification associated with the goods, data input into the computer can be simplified. The quantities of goods placed in each container can also be entered through the input devices described or manually through a numeric key pad. The client computers 401 may also be coupled to a radio frequency verification receiver 414 that is placed by the hangers 415 and used to check the transmissions from the transmitter 407. When the transmitter 407 emits the data packets, the verification receiver 414 detects the signals to determine if the hangers 415 were also likely to receive the data packets. If the verification receiver 414 does not detect the data packets there may be a failure within the system. The client computer 401 may retransmit the radio frequency packet and if the signals are repeatedly not detected by the verification receiver 414, the system can be reset and retested. Continued failure may cause the system to issue an error message to the operator.

One or more storage structures 411 can be placed within the transmission range of the transceivers 403. The storage structures 411 can include a plurality of substantially horizontal rails 419 which provide a storage area for the modular hangers 415. The storage structures 411 can also provide electrical power to the assembled modular hangers 415 stored on the rails 419.

In an embodiment each modular hanger 415 can include: a hook unit 418, a storage unit 421, and one or more indicator lights 417. The hook unit 408 and the storage unit 421 can be coupled together to form the assembled modular hanger 415 when ordered goods are placed in the storage unit 421. The assembled modular hangers 415 are placed on the rails 419 until the goods are removed from the storage unit. After the goods are removed, the modular hanger 415 can be disassembled by separating the hook unit 408 from the storage unit 421. Each modular hanger 415 may also include: an RF transceiver, an electronic memory storing a hanger address and a bar code that corresponds to the hanger address.

In a basic mode of operation, the storage units 421 can each include a bar code 422 and an electronic memory for storing the hanger address and other additional information. For example, the memory may store information about the goods or customer information. Goods are placed in the storage units 421 and the addresses of the hangers and the quantities and identifications of the goods placed in the associated storage units 421 are input and stored in the computers 401 memory or a database 412 accessible by the computers 401. Thus, the hanger address associated with any ordered goods can be identified. In an embodiment, the hanger addresses are also associated with a bar code 422 that is attached to or marked on each of the storage units 421. These bar codes 422 can be read with a bar code reader 409. Thus, rather than inputting the hanger addresses manually, the user can simply scan the bar code 422 with a bar code reader coupled to the computer to enter the hanger address information. In other embodiments various other possible input devices 416 can be used to read codes associated with the hanger addresses. These other input devices 416 can include optical scanners, RFID tag readers, magnetic strip readers and other suitable data input devices.

The description of goods or order can be a name of the goods, a description or a code representing the goods or order. Codes representing goods can be standardized within an industry and include: Stock Keeping Units (SKUs), Universal Product Code (UPC), National Drug Code (NDC), European Article Number (EAN), Global Trade Item Number (GTIN) Australian Product Number (APN) or any other goods codes. The goods and the addresses of the hangers are associated with each other and this information is stored on a database 412 that is accessible by the client computers 401. If the storage units 421 are filled remotely, the goods and hanger address information can be transmitted to the computers 401 in the storage area through a network, a portable memory device or any other suitable data transfer means.

If the storage units 421 have been filled with the goods in a remote area, such as a central filling center, the storage units 421 can be moved to a local storage area for pick up or distribution. At the storage area a hook unit is attached to each of the storage units 421 to form an assembled modular hanger 415. The modular hangers 415 are then placed on the storage rails 419. In an embodiment, each of the modular hangers 415 emits a wireless RF signal that includes the hanger address when the hanger 415 is placed on the rail. For example, the wireless signal can be an RF signal transmitted by a transceiver in the modular hanger 415 to the transceiver 403 coupled to the computers 401. The computers 401 can compare the hanger address with the listing of goods and hanger addresses to confirm that the goods have been received and are in stock. The computer 401 can also transmit an automated notification to the purchaser of the goods informing them that the goods are in the storage area.

When a customer goes to the storage area to pick up the goods, information about the goods, such as an order number, prescription, invoice, information associated with the goods, customer information, etc., is input into the computer 401 and if the goods are in the storage area, the computer 401 will emit a hanger address corresponding to the requested goods. The modular hangers will receive the hanger address and if the addresses match, the modular hanger will illuminate the indicator light. The modular hanger 415 can then be retrieved and the goods can be removed from the storage unit 421 and given to the customer. The storage unit 421 can also be separated from the hook unit to disassemble the modular hanger 415. The storage unit 421 can then be returned to the remote filling center to be reused.

Figure 5:
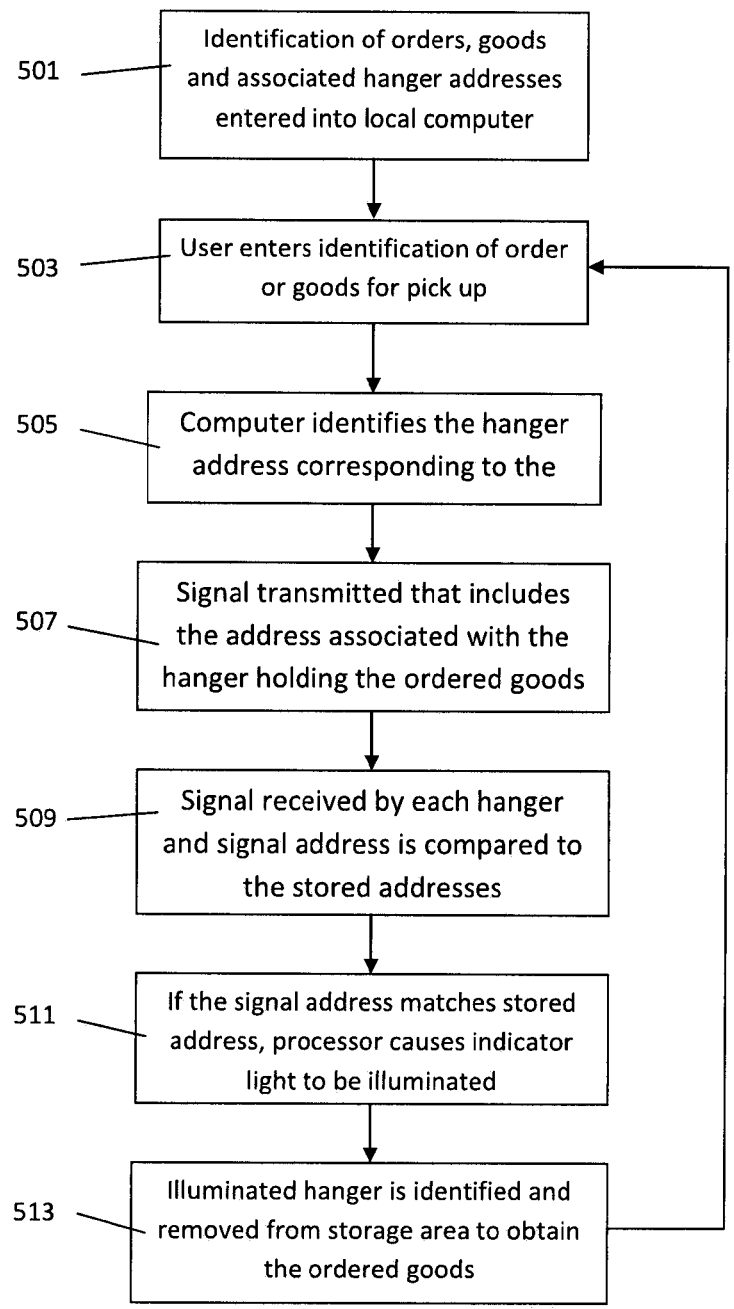
FIG. 5 is a flow chart for retrieving orders stored in modular hangers.

With reference to FIG. 5, a flow chart of the basic process used to locate goods in the local storage area is illustrated. As discussed above, an identification of goods and the associated hanger addresses are entered into the computer 501 and stored on a database. When someone needs to obtain the goods, the identification information for the goods is entered into the computer 503. The identification information can be a prescription, an invoice number, an order number, etc. The quantity of goods may also be entered. The computer identifies the address corresponding to the goods through the database 505 and transmits a signal through the RF transmitter such as a data packet that includes the hanger address associated with the hanger holding the goods 507. The RF signal data packet is received by transceivers in each of the modular hangers in the storage area. Each of the modular hangers may perform a data check to determine if the received packet has been corrupted. If the data is corrupt, the incoming packet can be discarded. If the data packet is not corrupt, the modular hanger compares the hanger address in the packet to their assigned addresses stored in the electronic memory 509. If there is a match, the modular hanger instructs the indicator light to be illuminated 511. The user can then easily find the illuminated hanger to obtain the desired goods 513 in the storage area. In some cases a single order may be stored in multiple hangers. Thus, the system will transmit data packets for each of the hanger addresses associated with the order and multiple hangers can be identified and illuminated at once.

In an embodiment, the inventive system can be used in installations where multiple goods stored in several different hangers are being picked simultaneously. In order to enable multiple hangers to be picked at one time, the illuminated indicator lights for each hanger must be a distinct signal to avoid mixing goods or orders. In this embodiment, the computer can transmit an illumination signal with the address signal through the RF transmitter to the hangers. The illumination signal can include a color and/or illumination pattern data. When the hanger receives the corresponding address signal, it can respond by illuminating the indicator light in the color and flash pattern corresponding to the illumination data.

Figure 6:
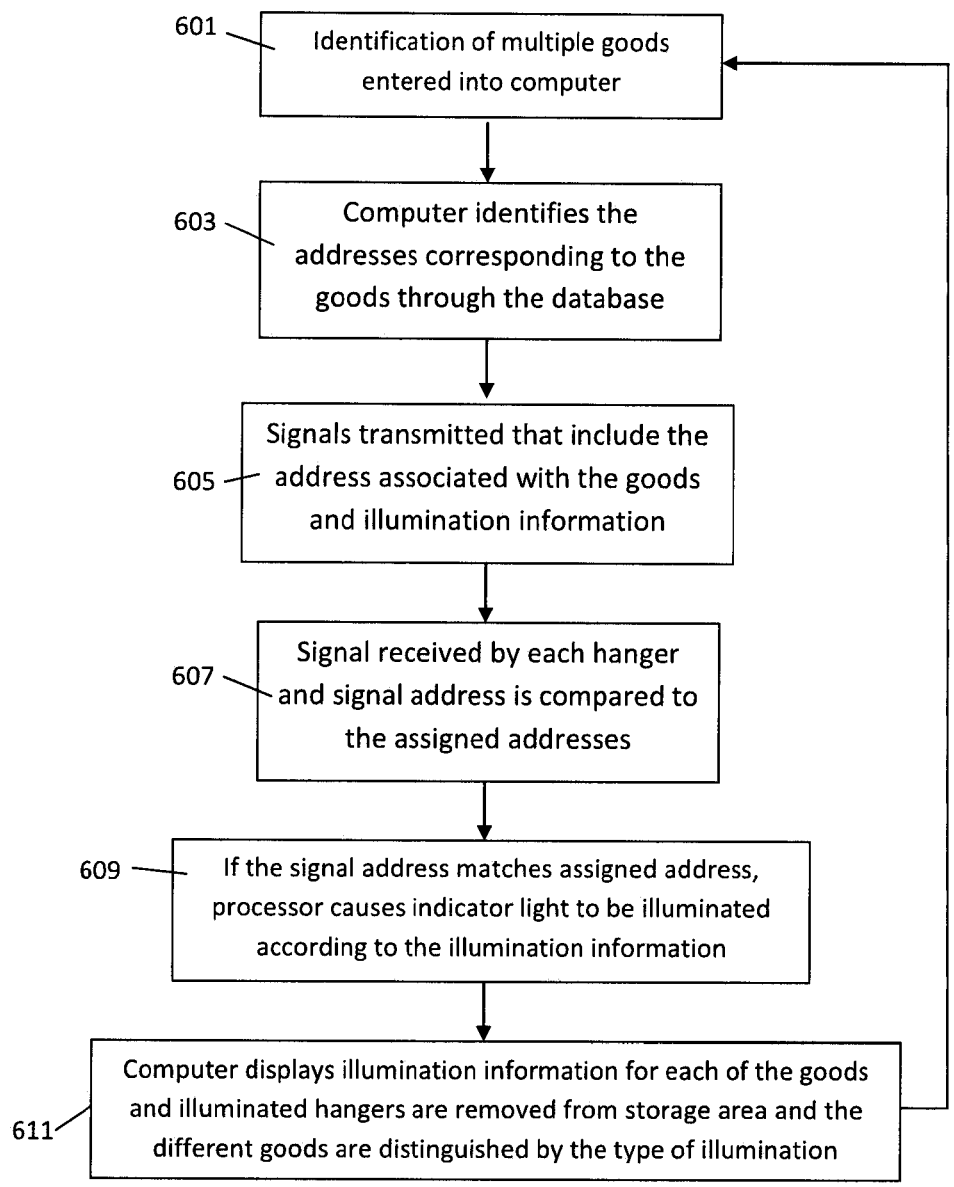
FIG. 6 is a flow chart for retrieving multiple orders stored in modular hangers simultaneously.

When multiple hangers are being picked up at the same time, the different colors can be used to distinguish the hangers which can each contain different goods. With reference to FIG. 6, when a user needs to find the goods or hangers, the user inputs identification information for each of the goods or hangers into the computer 601. The client computer uses the identification information to identify the hanger addresses associated with the goods through a database 603. The client computer then controls the RF transmitter to emit multiple RF signals that can be data packets. Each data packet can include a different address and a distinct illumination instruction 605. The client computer will also inform the worker which color is associated with each good or order being located. For example, if a first patient needs pain medication and a second patient needs indigestion medication, the client computer may transmit a first address for aspirin with a red illumination signal and a second address for antacids with a green illumination signal. The hangers will receive each of the data packets and compare the addresses received to the assigned address 607. If the address in the data packet is an exact match, the hanger will illuminate the indicator light in the accordance with the illumination instructions 609. The client computer will inform the worker that the hanger with the red light is aspirin and the hanger with the green light is antacids so that the worker will be able to identify and distinguish the hangers 611. Using this feature, multiple ordered goods or medications can be easily identified obtained from the storage area and given to the proper customers.

With reference to FIG. 4, in order to produce a light color, the indicator lights 417 may include separate red, green and blue (RGB) lights that are placed in close proximity of each other to form a single light output. By controlling the output of each of the red, green and blue lights, many different colors can be emitted by the indicator light 417. Thus, if multiple hangers receive corresponding address signals, each can produce different illumination outputs so the hangers are not mixed. In other embodiments, other types of multicolor lights can be used, such as a red, yellow, blue (RYB) light emitting diode (LED).

Another method for differentiating the hangers based upon illumination patterns is through variable pulses in the illumination. Various illumination patterns can be output based upon a repeating sequence of for example, 16 time slots which can each represent 125 milliseconds. The first goods can be in a hanger that emits a sequence of evenly timed pulsed illuminations each lasting about 1 second on and 1 second off. The second goods can be in a hanger that emits a faster series of pulses that last 0.25 seconds on and 0.25 second off. The computer can indicate the illumination pattern so the hangers can be identified and distinguished based upon the illumination patterns. In other embodiments, the illumination instruction can include a combination of different colors and pulse patterns. Because the flash patterns and colors are very distinct, a worker will be able to match the different illuminations to the different ordered goods.

By informing the user of the illumination color and flash pattern, the hanger containing the desired goods can be located and removed from the storage area. The container attached to the hanger can be open and the goods can be removed individually or all goods in the whole hanger can be inspected so that the order can be checked for accuracy. The delivery of goods can be recorded on the computer so that the identity and quantity of goods can be accounted for. Additional information such as time of delivery and recipient identification can also be recorded. After the desired goods are removed, the hanger can be disassembled by separating the storage unit from the hook unit. The hook units can be reattached to new storage units that have been filled with goods. The storage units can be refilled at the storage area or transported back to a central filling center where the same or different goods can be placed in the containers and revised goods information can be associated with the hanger address and input into the computer database.

The system may also have specific flash patterns to indicate errors or normal operation. For example, in an embodiment, a test signal can be transmitted which includes hanger addresses stored in the local computer database. The test signal may be recognized by the hangers and rather than illuminating the indicator light in response, they can be programmed so that only the modular hangers that did not receive their hanger address can illuminate their indicator lights. These hangers represent hanger that are on the storage rails but have hanger addresses that are not in the system. These hangers can be removed and rechecked to determine why they are not in the local computer database.

Figure 7:
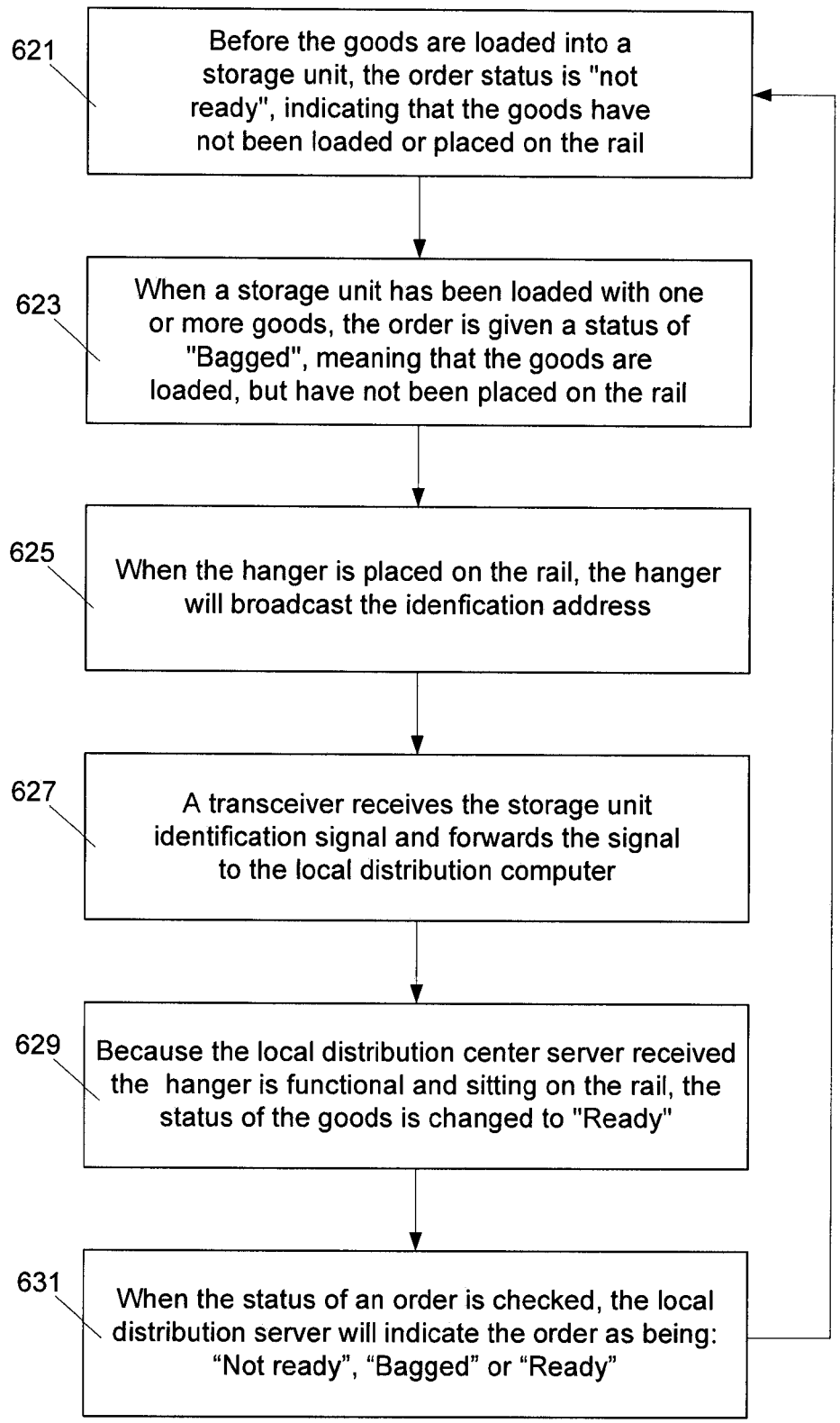
FIG. 7 is a flow chart for identifying the status of goods.

In addition to normal operations, the inventive system may also be able to provide status information for all orders. For example, each order can include a status such as: not ready, bagged and ready. With reference to FIG. 7, before an order is bagged, the system can determine that the order was placed but the goods have not been placed in a bag. Thus, the status can be "not ready" 621. When the bag is loaded with one or more goods, the worker can scan both the goods and the storage unit. With this information the system can update the status of the order to "bagged" to indicate that the goods have been placed in a storage unit but have not been placed on a rail 623. When the storage unit has been coupled to a hanger and the hanger has been placed on the rail, the hanger will broadcast the storage unit address 625. The local distribution center server receives the identification signal from the hanger and changes the status of the order to "ready" 629. This information can be made available to the customer. When the status of an order is checked through the local distribution center computer, the system will indicate that the order has a status of "not ready" "bagged" or "ready" 631. Orders that are either "not ready" or "bagged" are not available for customer pick up. This process is repeated for each of the goods placed on the rail.

If the order has been received by the local distribution center but the status has not changed to "ready" after a predetermined period of time, this may indicate that the order is in the local distribution area but not on a rail or the hanger is not in electrical proper contact with the conductors on the rail. In an embodiment, it may be possible to have all hangers that are in proper contact actuate their indicator lights simultaneously so that any hangers that are not in proper electrical contact can be easily identified. Workers can look at the hangers and find any hangers that are not illuminating their indicator lights. These hangers can be removed from the rail and checked. The hanger can be cleaned, repaired or replaced before the goods are placed back on the rail.

Figure 8:
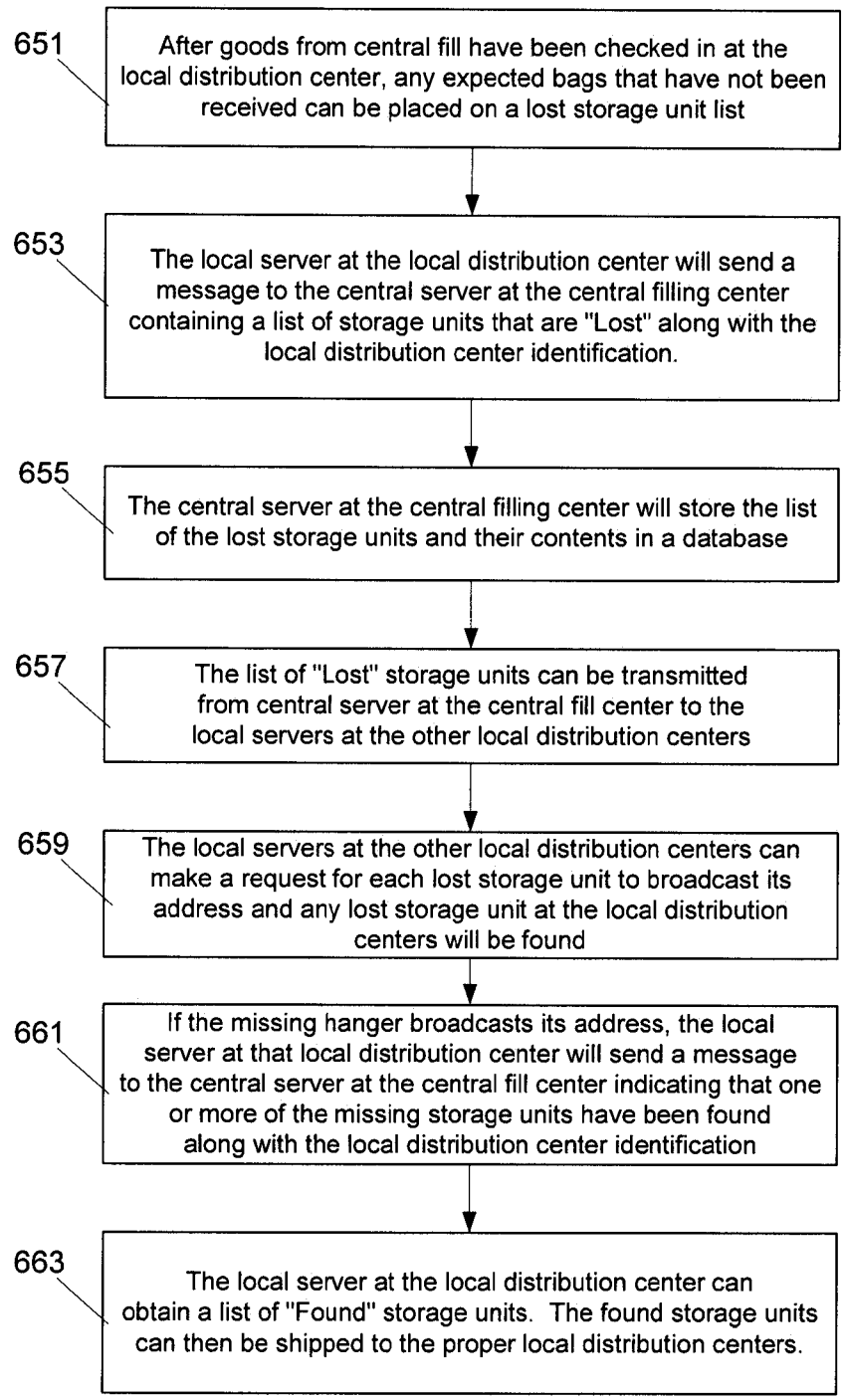
FIG. 8 is a flow chart for finding lost goods.

The inventive system can also be used to help locate lost or missing storage units of goods. With reference to FIG. 8, after items from central fill have been checked in at a local distribution center, any remaining bags that have not been checked in will be reported on a list of missing storage units 651. Through a GUI, a system user can mark any missing storage units as "Lost" and the local distribution server computer can send a message to the central fill server containing a list of goods that are "Lost" along with its store identification 653. The central fill server computer can store the list of the lost storage units and their contents in a database 655. The central fill server computer can then transmit a listing of the lost storage units to the other local distribution center servers 657. The local servers can review the list of "Lost" bags from central server at the central fill center. The lost storage units may have been placed in the storage areas of the other local distribution centers. In order to find the "Lost" storage units, the local servers at each of the local distribution centers can each transmit requests for each lost bag by broadcasting the addresses of the lost storage units. If the missing hanger responds to the lost bag address, the missing storage unit can broadcast its address back to the local server at that local distribution center and illuminate a light so that the lost storage units can be picked up 659. The local server can then send a message to the central server at the central fill center indicating that it has the missing storage unit. The central fill server can then update the status of the "Lost" prescription to "Found." The local distribution center can obtain the "Lost" goods and send these goods to the central fill center or directly to the proper local distribution center 663. Because all actions are transmitted to the central and local servers, the system operator can see the location that the storage unit was accidentally sent to the wrong local distributor and have the lost bags returned to the central fill center so that it can be sent to the proper distribution center.

Figure 9:
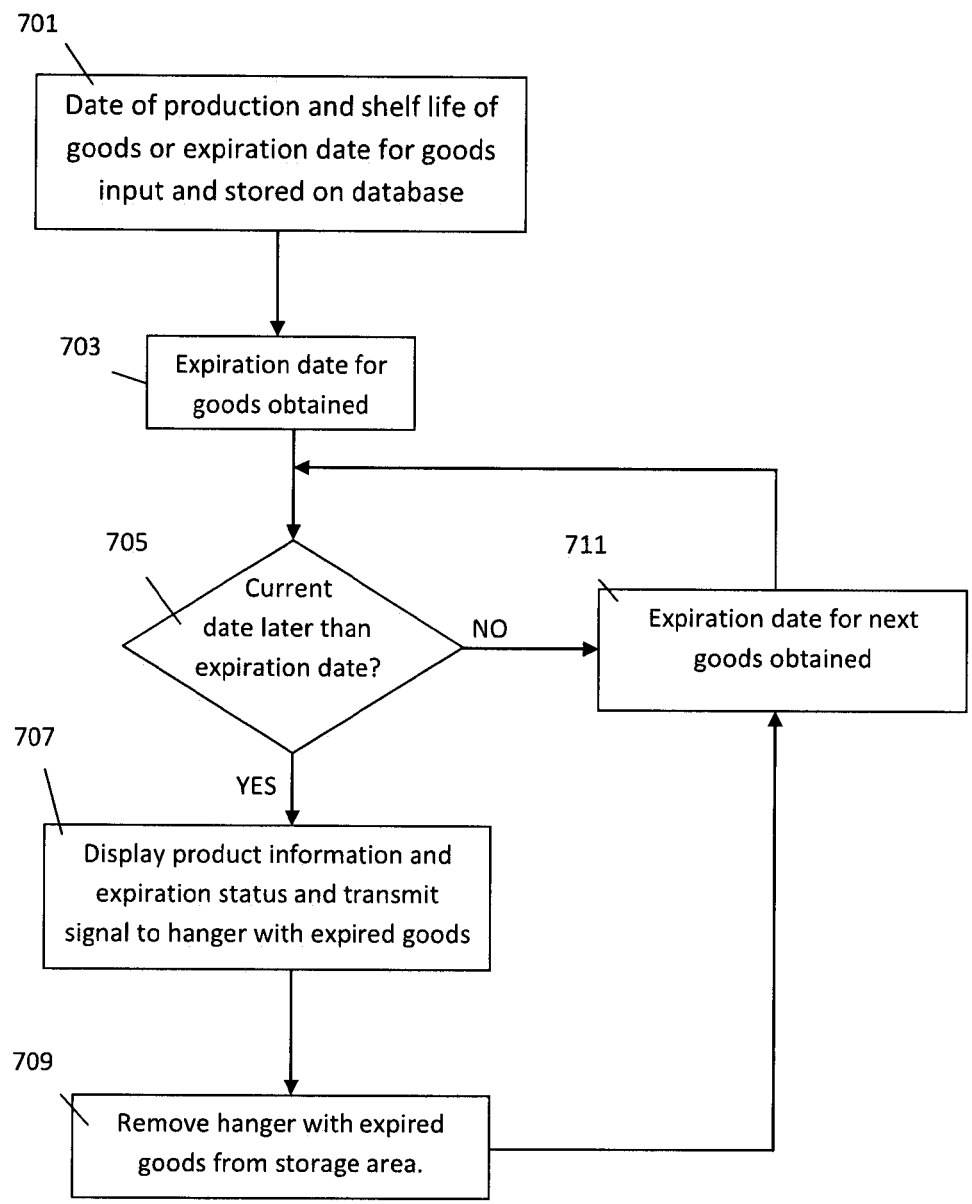
FIG. 9 is a flow chart for removing expired goods.

The inventive system can also perform additional tasks and store additional information about the goods placed in the storage units. This information can be used by the system for various purposes. For example, the goods placed in the storage units may have been part of an order picked from an inventory area for customer pick up. If the customer decided not to or forgets to pick up the goods, the system may be configured to have the goods restocked after a predetermined period of time. Many goods such as food or medication also have a limited shelf life. In an embodiment, the inventive system can be used to prevent the distribution of expired goods as illustrated in the flowchart shown in FIG. 9. In order to avoid distribution, the date of production and shelf life can be stored on the computer database 701. The computer can then calculate the expiration date and compare the current date to the expiration date. The computer may continuously check the status of each good having an expiration date 703. If the expiration date or a predetermine time prior to the expiration date has passed 705, the computer can inform the user that the certain goods have expired and need to be removed. The inventive system can transmit a signal that includes the hanger address associated with the expired goods and provide a visual display message on a screen that the goods are expired 707. The worker will be alerted to this problem and remove the illuminated hangers that contain the expired goods 709. In an embodiment, the expired goods can have a designated illumination color or pattern. For example, a solid red light may indicate that the goods coupled to the hanger are expired. The worker can then replace goods with fresh goods and input the revised information for the new goods into the computer database. If the expiration date has not expired, the system will proceed to the next goods having an expiration date 711. In the preferred embodiment, the system will check all goods having an expiration date on a daily basis. The expired goods may be removed from the storage area and destroyed or returned to the central fill center for proper processing.

There can be various other circumstances where goods need to be returned to the central fill center. For example, it is possible for some goods to be ordered and shipped to the local distribution center but never picked up by the customer. It is also possible that goods were accidentally shipped to the wrong local distribution center. In these situations, the goods can be returned to the central fill location for processing. In an embodiment, there can be a "Pre-Return To Stores" (Pre-RTS) process and a "Return To Stores" (RTS) process.

Figure 10:
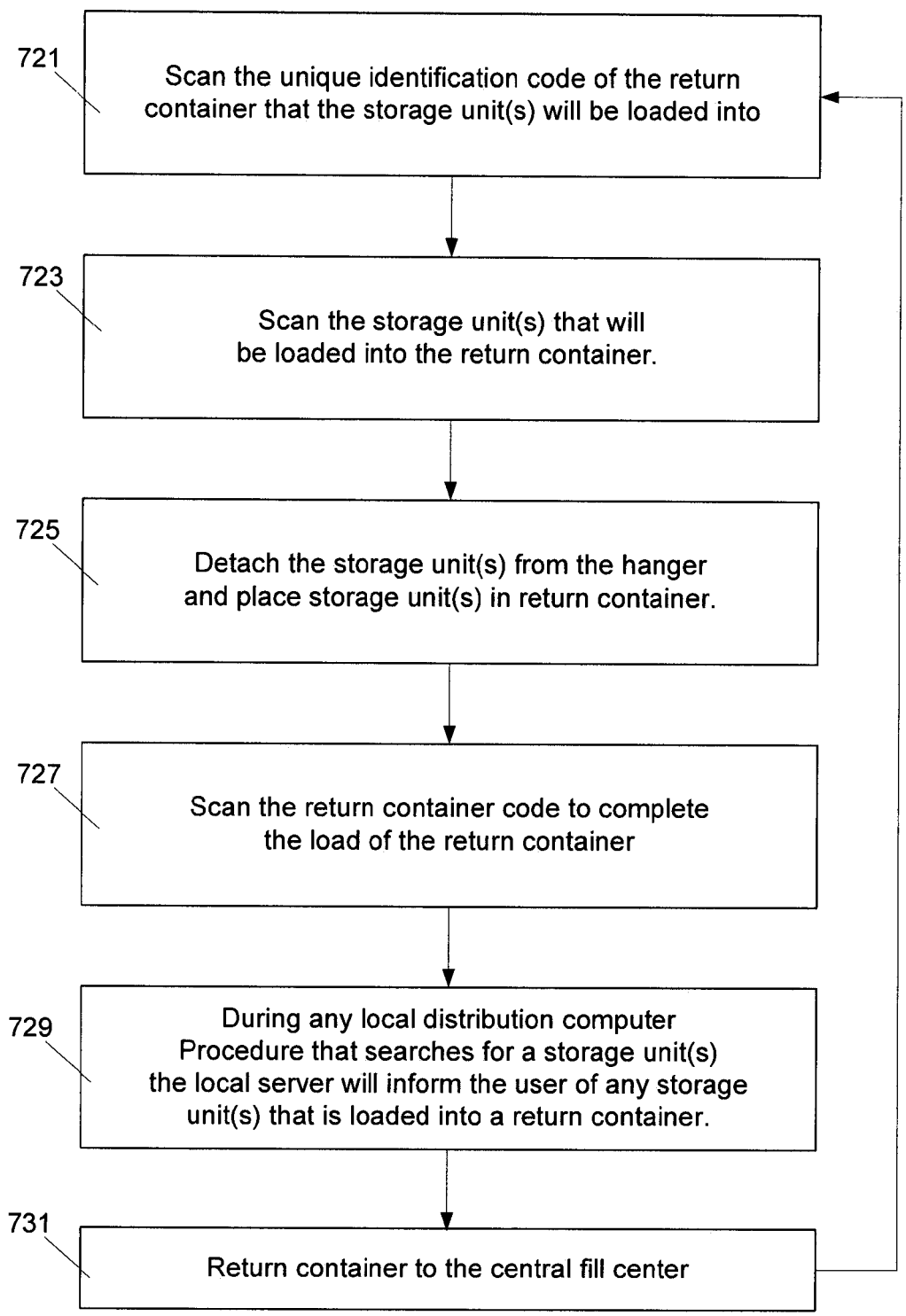
FIG. 10 is a flow chart for pre-returning to stores at the central fill center.

With reference to FIG. 10, when goods need to be sent back to stores at a central fill location, the Pre-RTS procedure can include, scanning the identification of the return storage container 721. The return shipping container can be a crate, tote or any other suitable storage structure that the return goods will be loaded into. The storage units containing the goods that are being returned can then be scanned 723. The hangers can be removed from the bags and the storage units can be placed in a return container 725. The return container can be scanned again to indicate that the return crate had been loaded 727. The return container will be stored in the local distribution center until it is shipped back to the central fill location. The local and central fill server computers can communicate so that each knows which goods and storage containers are in each return shipping container and the locations of the return containers. If anyone attempts to obtain the goods from a local distribution center before the return container has been shipped back to the central fill location, the computer will inform the worker that the requested goods are in the return container 729 and the requested goods can be retrieved. After a predetermined time or after the return container is full, the return container will be shipped back to the central fill in a returned to stores (RTS) process 731 and the Pre-RTS process can be repeated.

Figure 11:
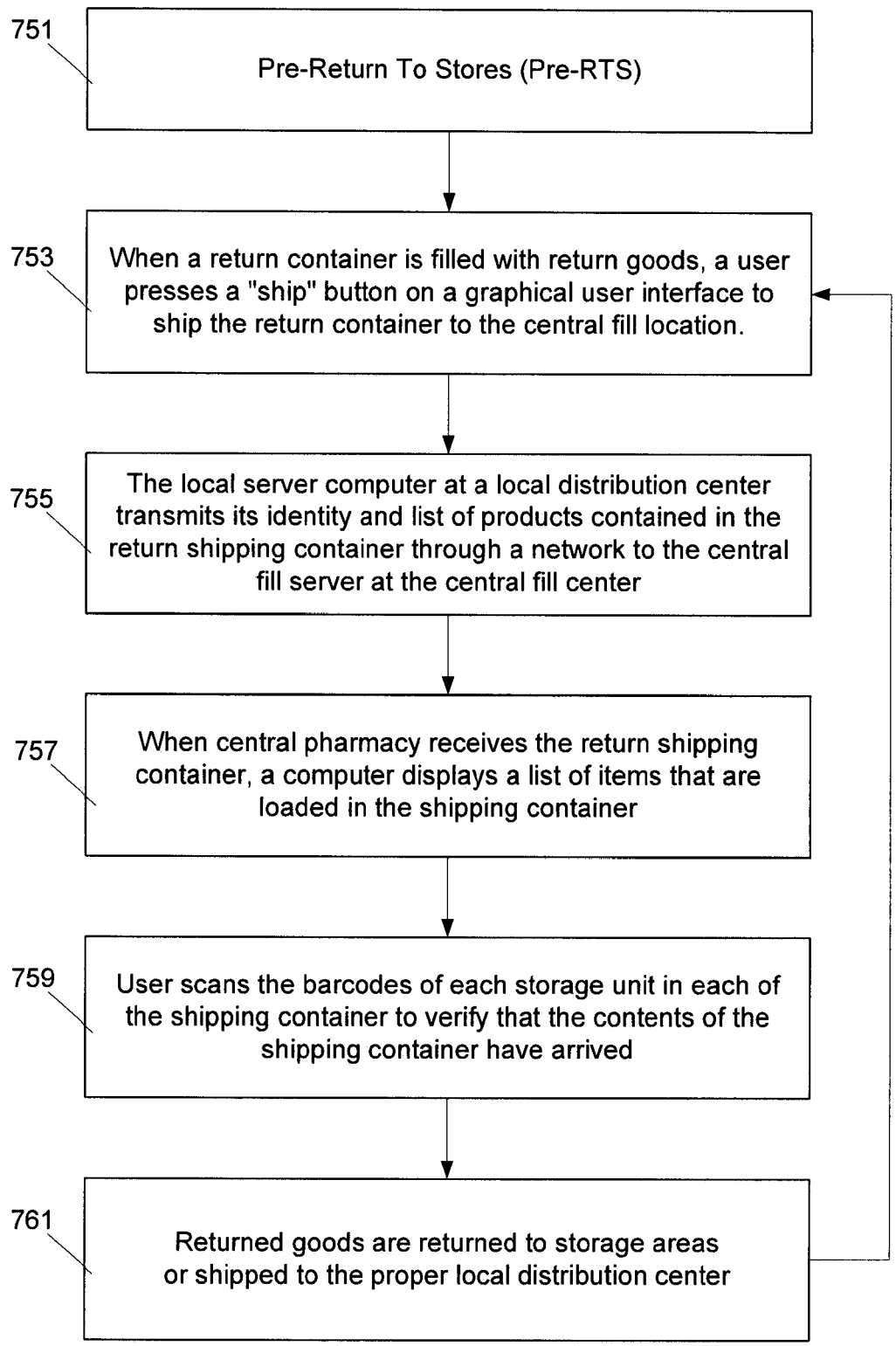
FIG. 11 is a flow chart for returning goods to stores at the central fill center.

With reference to FIG. 11, an embodiment of a return to stores (RTS) process is illustrated. The Pre-RTS process is completed 751 and all bags to be returned are placed in the shipping container, the container can be scanned. When the storage units with the return goods is filled and ready for to be sent back to the central fill center, a user can press a "ship" button on a graphical user interface and the container can be sent to the central fill center 753. The local distribution center computer can then transmit a listing of the goods that are being returned and the identification of the local distribution center that is returning the goods to the central fill computer 755. When the return container is received by the central filling center, the return container is scanned and the corresponding list of goods being returned is displayed 757. The storage units containing the received goods are scanned and the contents of the storage units are compared to the listing of goods transmitted by the local distribution computer to verify that all of the returned goods have been received 759. The returned goods can then be returned to their proper storage area or shipped to the proper local distribution center 761.

If there are discrepancies between the listing of returned goods transmitted to the central fill server and the returned goods that are actually received, the listing of returned goods can be manually updated based upon the goods that have been received. Once the storage container is returned to the central fill location, the computer will inform the worker that the goods were returned to stores and are no longer available at the local distribution center. The customer may obtain a refund and/or reorder the goods. If the goods have an expiration date that has expired, the expired goods can be properly processed.

In the preferred embodiment, the inventive system utilizes special hardware components that allow the system to function as designed. In the preferred embodiment, the hangers include electrical components that are powered by an external power source that is coupled to the storage rails. In order to perform the power transfer, special components are utilized that include electrical contacts that allow power to be transferred from the external power source through the rods in the storage area to each of the hangers.

Figure 12:
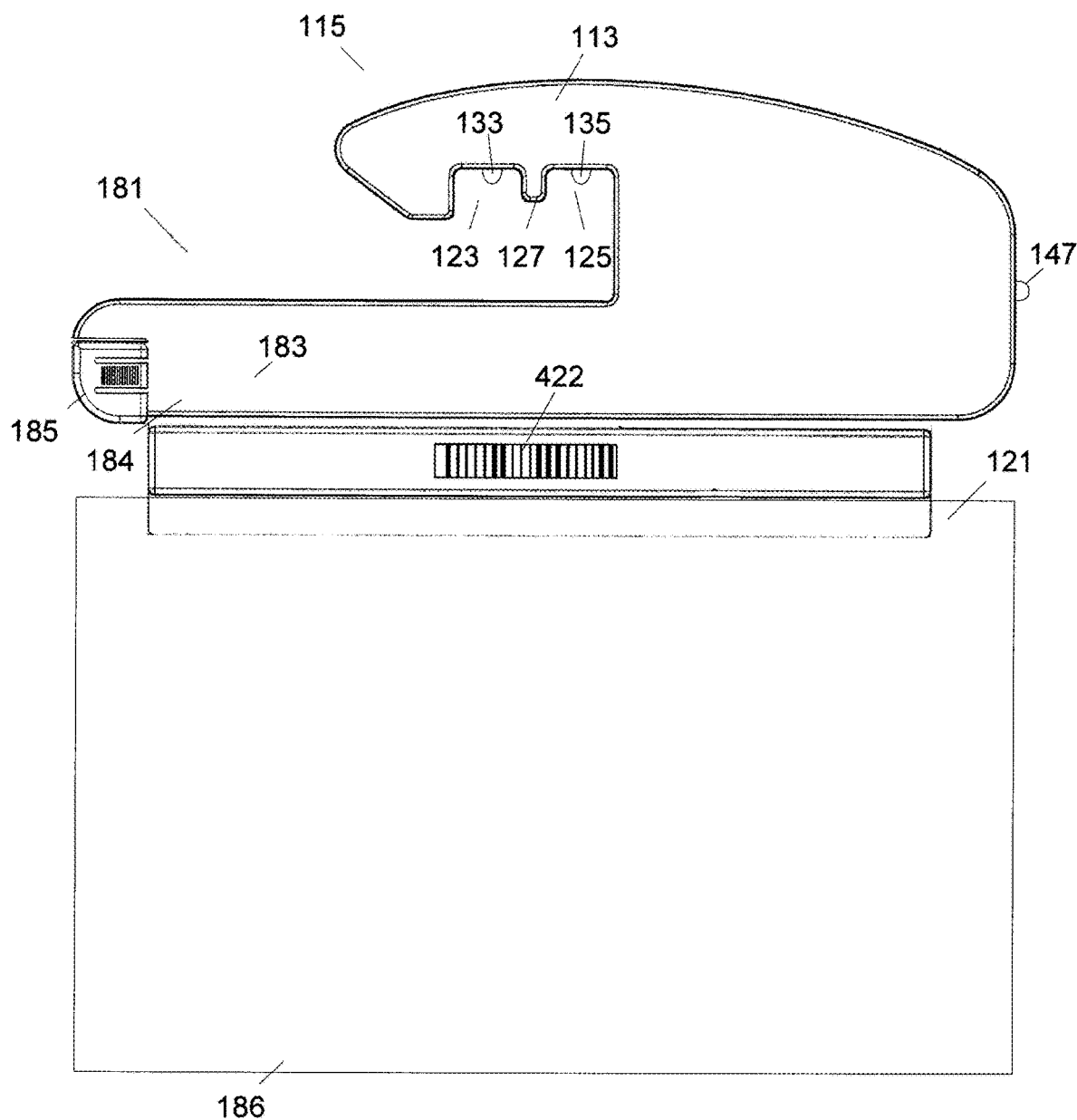
FIG. 12 is a view of an embodiment of an assembled modular hanger.
Figure 13:
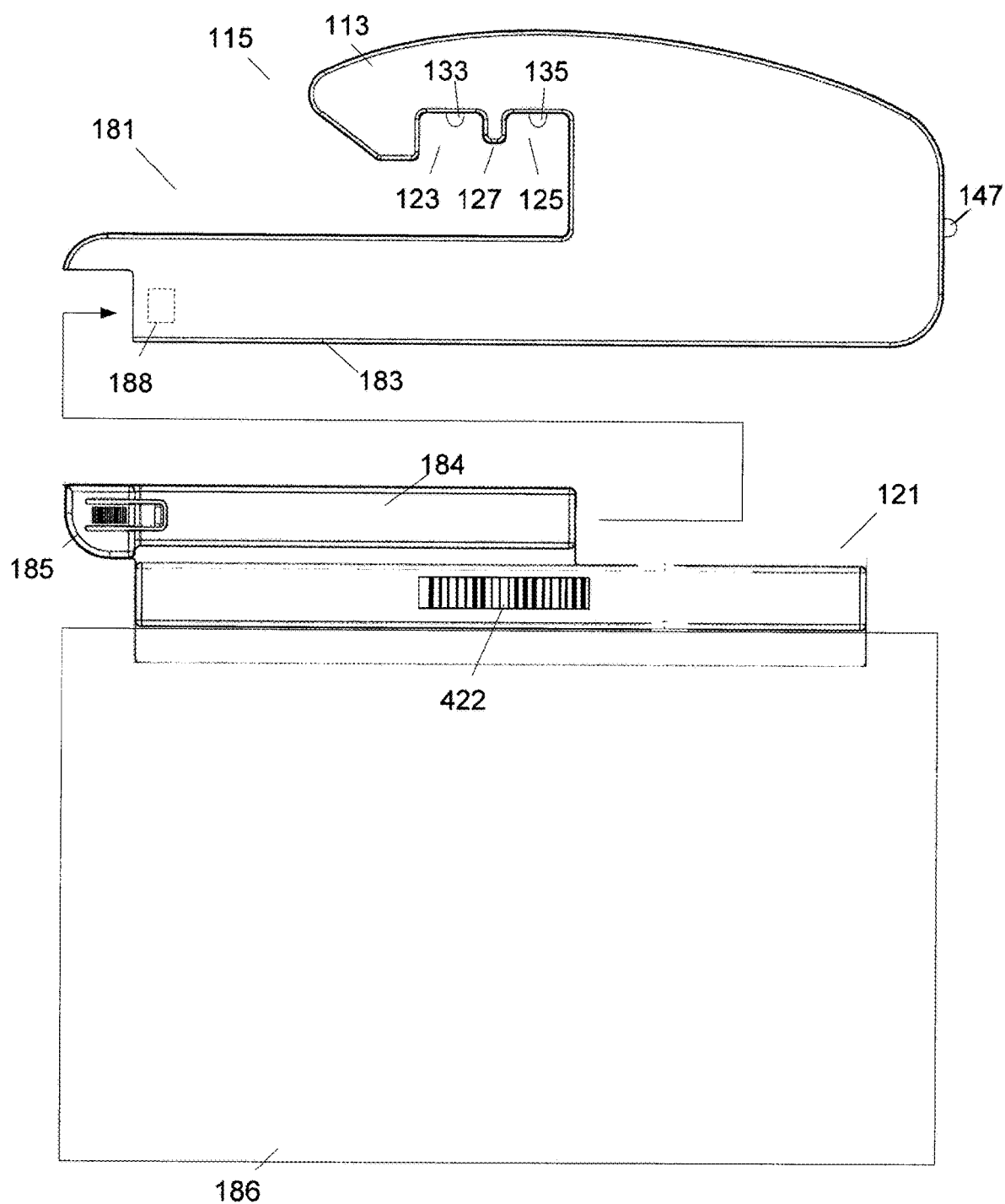
FIG. 13 is a view of an embodiment of a disassembled modular hanger.

With reference to FIGS. 12 and 13, an embodiment of the modular hanger 115 is illustrated. The modular hanger 115 can include a hook unit 181 and a storage unit 121. FIG. 12 illustrates the modular hanger 115 in the assembled configuration with the hook unit 181 coupled to the storage unit 121 and FIG. 13 illustrates the modular hanger 115 with the hook unit 181 separated from the storage unit 121. The hook unit 181 can include a hook portion 113 that has a first recessed area 123 that is separated from a second recessed area 125 by a tab 127. In an embodiment, the hanger 115 can have a first electrical contact 133 that extends into the first recessed area 123 and a second electrical contact 135 that extends into the second recessed area 125. An indicator light 147 can be attached to an end of the hook unit 181 and a first coupling 183 can be attached to the bottom of the hook unit 181.

The storage unit 121 can include a second coupling 184, a locking mechanism 185 and a storage container 186 for storing the goods. The storage unit 121 can be coupled to the hook unit 181 by sliding the second connector 184 into the first connector 183. When the second coupling 184 is fully inserted into the first coupling 183, the locking mechanism may engage a locking feature 188 of the first coupling 183 to lock the storage unit 121 to the hook unit 181 to prevent the accidental separation. When a user wishes to separate the storage unit 121 from the hook unit 181, the user can squeeze the locking mechanism 185 to release the locking mechanism 185 from the locking feature 188 of the first coupling 183. The user can then separate the hook unit 181 from the storage unit 121.

Figure 14:
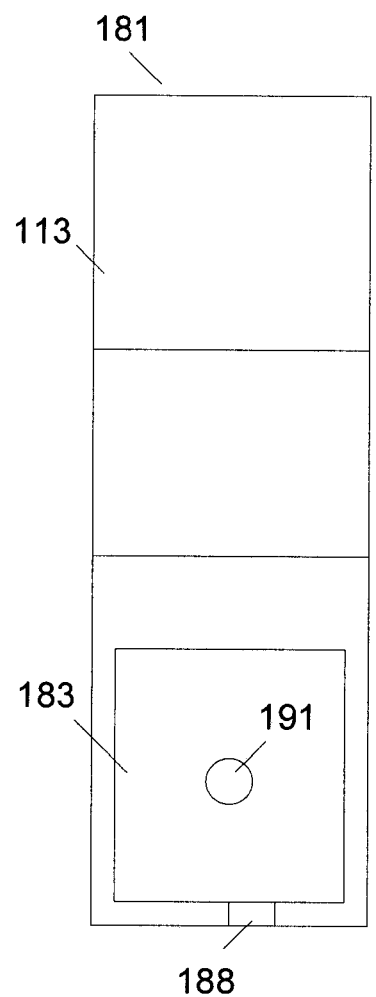
FIG. 14 is a front view of the hook unit.
Figure 15:
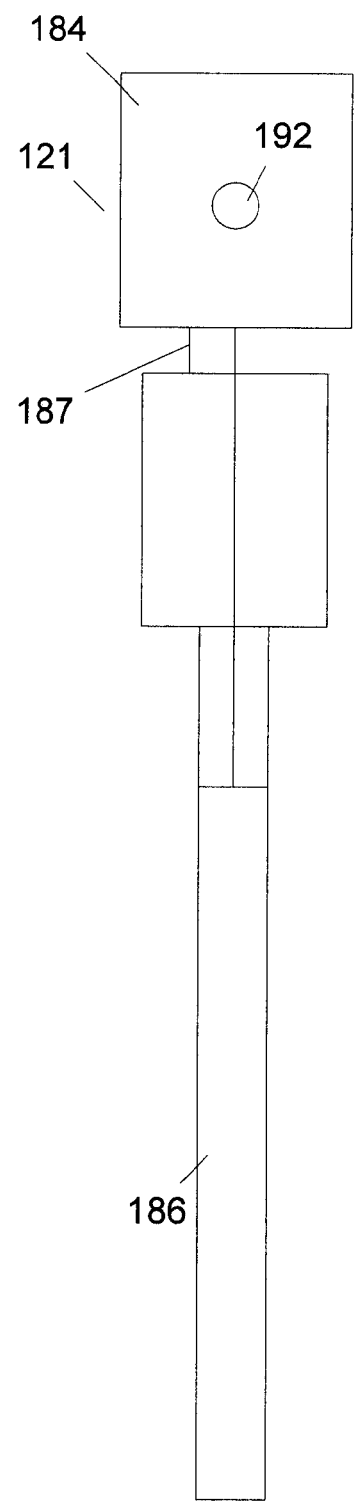
FIG. 15 a rear view of the storage unit.

FIG. 14 illustrates a rear view of an embodiment of the hook unit 181 and FIG. 15 illustrates a front view of the storage unit 121. In the illustrated embodiment, the second connector 184 can have a rectangular cross section and the first connector 183 can have a corresponding rectangular cross section recessed volume. A thin tab 187 can be attached to the bottom of the second connector 184 and the top of the storage container 186. When the first connector 183 is inserted into the second connector 184, the tab 187 can slide into the slot 188 in the bottom first connector 183. The lower surface of the second connector 184 rests against the internal lower surface of the first connector 183 and this contact area supports the weight of the storage unit 121 and the goods in the storage unit 121. In other embodiments, the cross section of the first connector 183 and the second connector 184 can be any other suitable shape, such as square, triangular, circular, etc.

Figure 16:
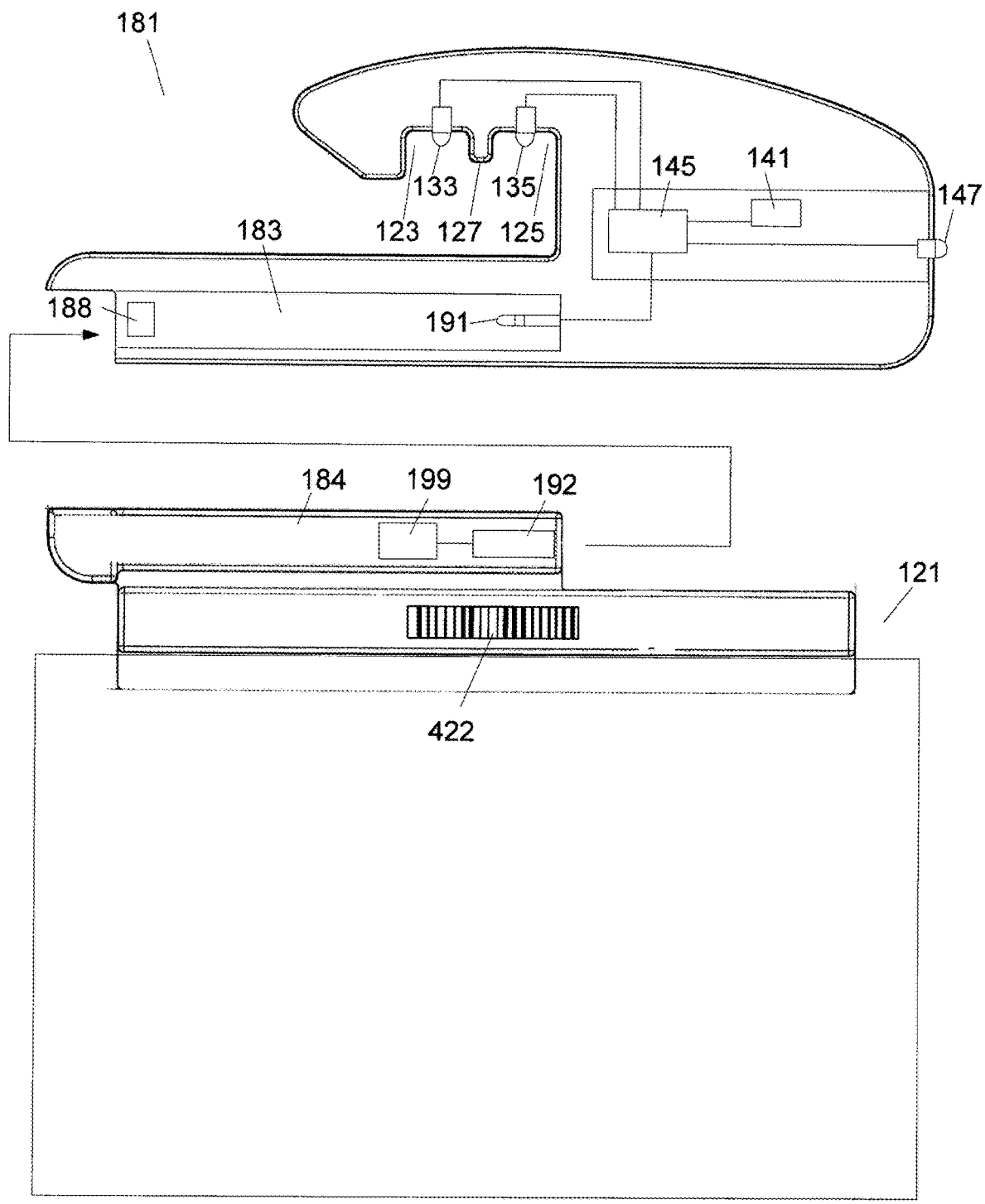
FIG. 16 is a cross sectional view of an embodiment of the modular hanger.

FIG. 16 illustrates a cross sectional view of an embodiment of the modular hanger 115. The hook unit 181 can include a microprocessor 145 coupled to an RF transceiver 141, an indicator light 147 and a first electrical connector 191. The first electrical contact 133 and the second electrical contact 135 can be coupled to the microprocessor 145 and provide electrical power. The modular hanger may not include any internal electrical power storage device and the electrical components may only be operable when the modular hanger 115 is placed on a storage rail which provides electrical power to the modular hanger 115. These electrical components are housed within the external shell of the hook unit 181 which protects the components. The storage unit 121 can include a second electrical connector 192 which is connected to an electronic memory device 199 such as an erasable programmable read only memory (EPROM), flash memory or any other suitable type of memory. These memory devices can store the hanger address even when electrical power is not provided.

When the hook unit 181 is attached to the storage unit 121, the second connector 184 is inserted into the first connector 183 and the first electrical connector 191 can connect with the second electrical connector 192. In an embodiment, the first electrical connector 191 can be a jack and the second electrical connector 192 can be a plug. In other embodiments, the first electrical connector 191 and the second electrical connector 192 can be any other suitable electrical connection mechanism. This connection of the first electrical connector 191 with the second electrical connector 192 electrically couples the memory 199 to the microprocessor 145. In an embodiment, all of the hook units can be the same and each of the storage units 121 can have a unique hanger address stored in the electronic memory. When the storage unit 121 is coupled to the hook unit 181, the electrical connection allows the hanger address stored in the memory 199 to be received by the microprocessor 145. The assembled modular hanger 115 can then transmit the unique hanger address in a signal through the transceiver 141. The hanger address signal can then be received by the computer transceiver to confirm that the goods are the storage area and ready for pick up.

When the stored goods are being picked up, the local computer will transmit an RF data packet that includes a hanger address associated with the order that is being picked up. The transceiver 141 receives the RF data packets that includes an address and forwards this information to the microprocessor 145 which compares the address from the RF data packet to the address stored in memory 199. The address can be a made up of four bytes of data represented by any number between 0.0.0.0 and 255.255.255.255. In other embodiments, any other suitable hanger address format can be used. If the address in the packet is an exact match for the stored address, the microprocessor 145 will emit a match signal which causes the indicator light 147 to be illuminated. If the RF signal has a hanger address is not an exact match, the microprocessor 145 will ignore the RF signal and the indicator light 147 is not illuminated.

In an embodiment, the electrical components may only be powered by an external power source. For example, the rails in the storage area can provide electrical power to the electrical components while the hanger 181 is stored on the rail. In order to provide electrical power, the hanger 181 can have electrical contacts 133, 135 that receive electrical power from the rail to power the RF receiver 141, microprocessor 145 and indicator light 147. In an embodiment, the hanger 181 can have a first electrical contact 133 that extends into the first recessed area 123 and a second electrical contact 135 that extends into the second recessed area 125. The hanger 181 can also include a tab 127 that can be an elongated straight structure that engages a groove in the rail and aligns the first electrical contact 133 and the second electrical contact 135 with electrical strips in the rail and improves the electrical contact.

Figure 17:
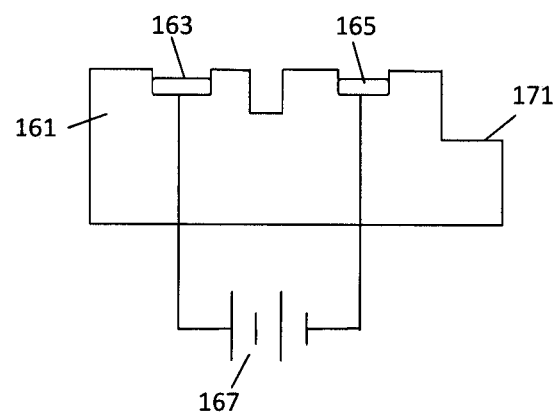
FIG. 17 is a cross sectional view of the storage shelf rail.

The electrical power is preferably a low voltage direct current, although in other embodiments an alternating current electrical power supply may also be used with electrical rectifier circuitry. With reference to FIG. 17, a cross section of a rail 161 for supporting the modular hangers is illustrated. The rail has two conductors 163, 165 that extend down the length so that the electrical contact will be maintained when the hanger is placed in any location along the length. Because the hangers are preferably setup for direct current, the negative power lead of the electrical power supply 167 can be coupled to one conductor 163 and the positive power lead can be coupled to the other conductor 165. A groove 167 is between the two conductors 163, 165 can be slightly wider than the tab of the modular hangers and when the tabs can fit within the groove 167 to hold the hangers at a substantially perpendicular angle to the rail 161. This aligns the electrical contacts with the conductors 163, 165 and insures proper electrical contact between the hangers and the rail 161. The electrical power supply 167 will typically provide electricity to several rails 161 which can be wired in parallel or in series.

Since applying a reversed polarity will damage the electrical components, the rail 161 may have a mechanism that prevents the hanger from being placed on the rail 161 incorrectly. For example, the rail 161 may have a tab 171 that extends from the back side and runs along the length of the rail 161. Since the hook portion of the hanger is only open on one side, the tab 171 would prevent the electrical contacts from contacting the conductors 163, 165 unless the hook is in the proper orientation relative to the rail 161.

In order to properly utilize the inventive system, the power requirements must be determined and provided to the hangers. In an embodiment, each of the hangers may require 250 mA of current and 3.6 DC volts. Each hanger may be 1.5 inches wide so a 48 inch shelf rail will be able to hold a total of 32 hangers. If there are 5 shelf rails on each rack frame each having 32 hangers there will be 160 hangers on each rack frame. The total current required for each rack frame will be 160×250 mA=40 amps and the power required will be 3.6 volts×40 amps=144 watts. The power supply must have an output that is larger than the power drawn by the hangers. If the system is powered by a single power source, in order to provide a safety factor, the power supply may be 20% or more than the power requirements. Thus, a 230 watt, 3.6 volt power supply will provide more than enough power for this exemplary system. In the preferred embodiment, a power transformer and rectifier are used to provide power to the system. The transformer may convert 110 volt alternating current to 3.6 volts of direct current. In other embodiments, other voltages can be used. For example, the hangers may operate at 12 volts and the rails may be coupled to a 12 volt power supply.

In an embodiment the inventive system can be configured to obtain confirmation of the communications and detect errors in the system. A client computer may attempt to transmit an address within a data packet through the local transceiver. However, the hanger with the matching address may not respond by illuminating the indicator light. A transceiver in the modular hanger can provide an RF confirmation signal of the receipt of communications between the system and the hanger. This allows the processing of the goods to be tracked by the system. For example, a computer coupled to a network may instruct the transmitter to emit a data packet that includes an address for a hanger. The data packet is transmitted and the hangers compare the address with the assigned address. The hanger having the matching address will then emit a confirmation signal with the corresponding address receives the data packet. The system can monitor the transmission and receipt of RF signals and based upon this information, the system can determine the status of each RF data packet. This information can be used to monitor the activities of the employees for example, the system may detect the time between orders being transmitted and goods being located.

In another embodiment, the modular hangers can be used to extend the range of the computer transceiver. For example, in an embodiment, a modular hanger can receive an RF signal from the computer with a hanger address. The address may not match the address stored in memory and the modular hanger may respond by retransmitting the computer's RF signal which may be received by other modular hangers that are outside the transmission range of the computer transceiver. By repeating this communications relay, the RF signal can be retransmitted throughout the hanger storage area.

Various other mechanisms can be used to check the operations of the inventive system. In an embodiment, the inventive system may perform periodic connection checks to determine if the system is operating properly. The system can have a mechanism to determine if the coupled system is properly coupled and communicating. The system check may be the transmission of a beacon which is a check signal transmission between the transceivers and the hangers. The beacon can be various predefined commands. For example, the beacon can be a command from the computer to the hangers to return communication packets back to the computer. The computer can transmit the beacon and then wait for the reply. If the reply is not transmitted, this can indicate that there is a problem with the hanger connection or transceiver. Alternatively, the beacons can be communication packets that are check signals that are only transmitted from each of the hangers to the computer. The system will listen for the communication packets from each hanger and if the beacon is not received within a predetermined period of time, the system will conclude that communications were lost between the computer and one or more of the hangers. The computer can then perform a reset process. The beacons may be transmitted once every 30 seconds and the system may reset if the communication packets are not received within 60 seconds. The transceiver can facilitate various other modes of operation.

In an embodiment, the hangers can each broadcast its address or any other message automatically when it is powered on by being placed on the power rail. This initial address or message signal can confirm that the hanger is functioning properly. If the system does not receive the address or other message signal, this can indicate that there is a problem with the hanger. In other embodiments, the hangers can each broadcast its address or any other message when the hanger receives a request from the system through the transceiver as described above.

Figure 18:
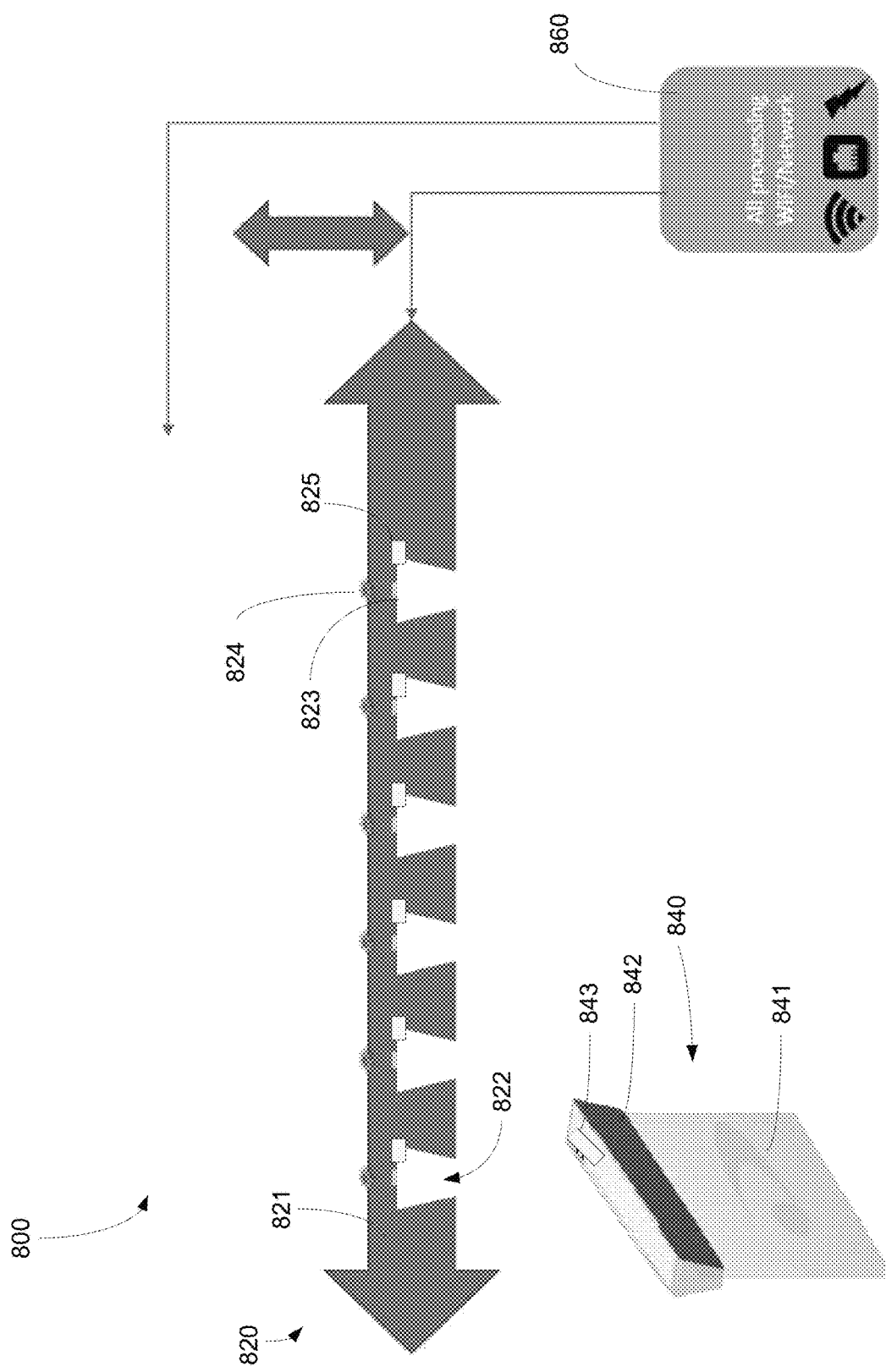
FIG. 18 is a schematic block diagram illustrating an alternative embodiment of a storage system.
Figure 19:
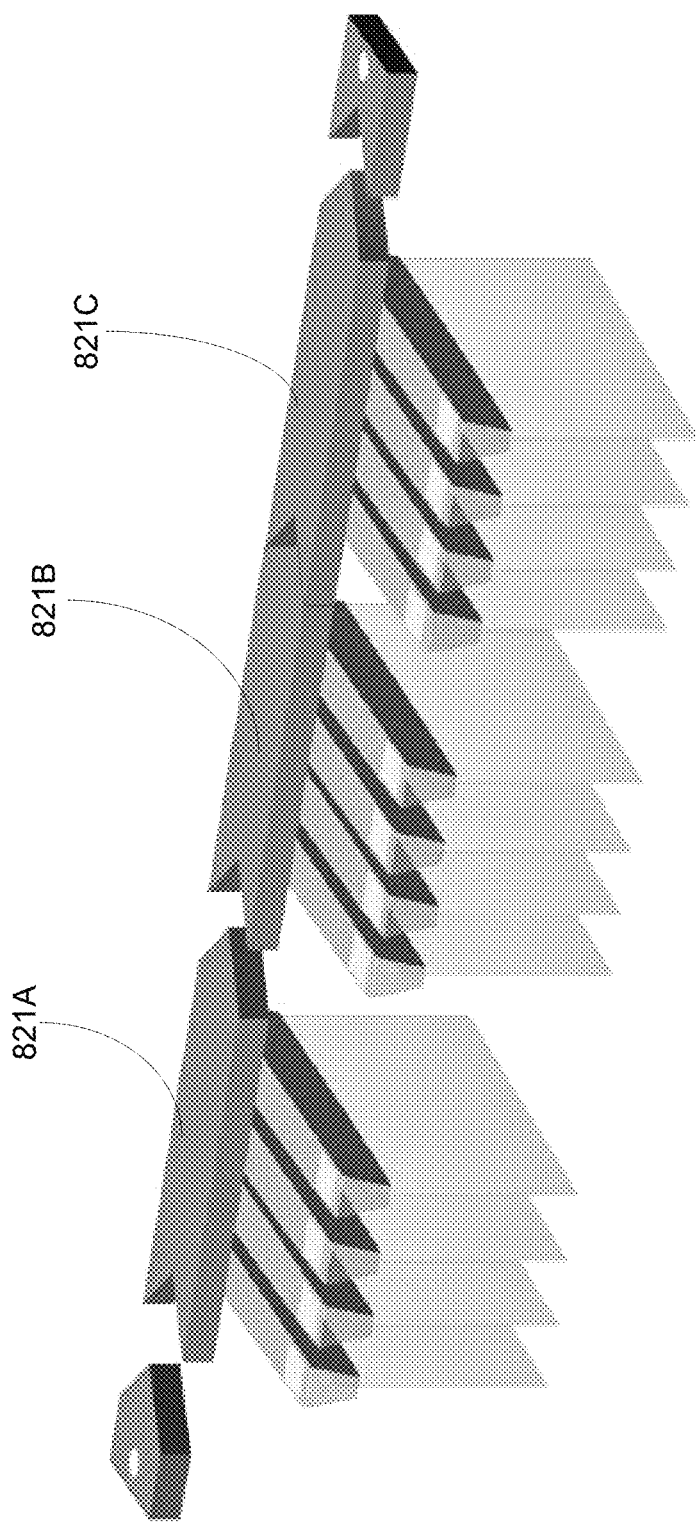
FIG. 19 is a schematic block diagram illustrating multiple interconnected sections of the storage system of FIG. 18.
Figure 20:
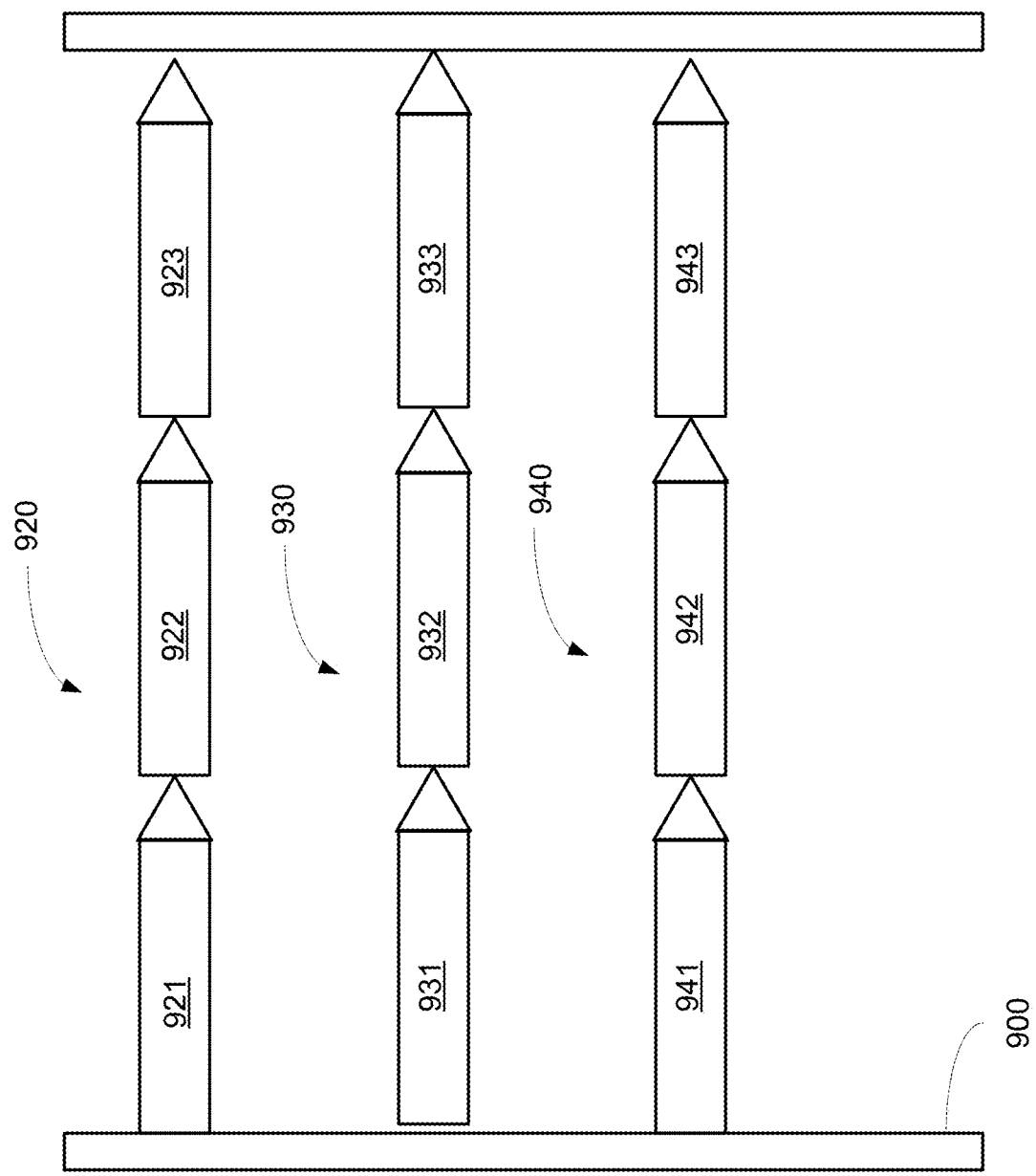
FIG. 20 is a schematic block diagram illustrating one arrangement of the multiple interconnected section of FIG. 19.

FIGS. 18-26 illustrate alternative embodiments wherein the intelligence of the system is incorporated into the rail assembly rather than into the hanger assembly. For example, FIG. 18 is a schematic illustration of a product storage system 800 for use in a storage facility, such as a pharmacy will-call space storing orders for prescription medicines for customers of the pharmacy. The storage system 800 is characterized by a rail 820 having a rail identifier ("rail ID") and having multiple slots 822, each slot being a defined location on the rail. A typical storage system will have multiple rails as part of a single local system managing local inventory.

Each slot 822 is identically configured in the rail 820 for (i) receiving and holding a compatible bag unit 840; (ii) recognizing and storing a bag unit identifier ("bag ID") affixed with the bag unit; and (iii) transmitting the bag ID, the rail ID, and the location, e.g., the specific slot number in which the bag is docked on the rail, to a master controller 860 for the local storage facility, where the inventory information for the storage facility is updated. For example, the specific location of the bag unit may be identified using a digital address that includes the rail ID and the slot number.

The rail 820 shown in FIG. 18 includes a physical structure 821 adapted to receive and hold bags 840 in place, and an electronic structure 880 (see FIGS. 22A and 22B) configured with physical circuitry, sensors, and programmable elements, to (1) provide power and control for the physical structure and its component parts; (2) sense bag placement, and identify and record the location corresponding to the bag placement; (3) obtain the bag ID; and (4) handle data communications between the rail and the controller 860. The physical structure and the electronic structure of the rail may of course take different forms, wherein the primary objective of the physical structure is to receive and hold bag units, while the primary objective of electronic structure is to identify the bag unit and report to the controller.

In general, a single rail may include multiple interconnected physical structures. For example, as shown schematically in FIG. 19, the physical structures can be formed as identical modular sections 821A, 821B and 821C that are inter-connected both mechanically and electrically. Each section 821A, 821B and 821C is configured identically with a physical structure and an electronic structure as described, with many aspects of the operation implemented through programmed instructions of the electronic structure for the section and for interacting with other sections as necessary as well as with the controller 860. End caps 828, 829 are placed at respective ends of the interconnected sections to facilitate mechanical mounting with a support structure. In one embodiment, the end caps could be configured to include electronic connections from the rail sections to or through the support structure.

It should be apparent that there could be a number of different arrangements of the physical structures, depending upon needs, space and implementation details for a particular application. For example, as shown schematically in FIG. 20, a storage structure 900 includes three sets of rails 920, 930, 940 arranged in a parallel orientation. Top rail 920 has multiple inter-connected sections 921, 922, 923; middle rail 930 has multiple inter-connected sections 931, 932, 933; bottom rail 940 has multiple inter-connected sections 941, 942, 943; and each section has bags docked thereon and is in communication with the master controller either through a wired connection (such as a common bus) or wireless connection.

Returning to FIG. 18, each slot 822 of the physical structure 821 includes a sensor 825 affixed to the rail in an appropriate position, the sensor configured to (1) detect that a bag has been placed into the slot, and to (2) identify the bag unit. Further, each slot 822 includes a first light emitting diode ("LED") 823 and a second LED 824 affixed with the physical structure. The first LED 823 is positioned to illuminate the bag unit 840 such that the sensor 825 can image the bag and its attached label. In the illustrated embodiment, the first LED 823 is positioned at the top of the slot 822. The second LED 824 is positioned on the top front of the physical structure 821 and is used to give a visual indicator to users, as previously described.

The bag unit 840 is simply a storage unit for goods configured to be used with the rail 820; that is, capable of being securely placed onto and removed from the rail. In one embodiment, the bag unit 840 is a plastic bag 841 having a suitable closure mechanism 842. The bag 841 may be made from a low-density polyethylene (LDPE) or a high-density polyethylene (HDPE) plastic material or other suitable materials, in varying sizes as needed, for example, as two opposing panels sealed on three edges, and the closure mechanism 842 affixed with the fourth edge. A heavier-duty plastic material could be used for larger or heavier loads, and paperboard/cardboard containers are also contemplated. A gusset-style bag could be used.

The closure mechanism 842 is typically a hard plastic structure integrated with the bag that is adapted to open and close one side of the bag, such as a zip-lock mechanism integrated at one end of the plastic bag In one embodiment, a label 843 is affixed with the bag unit, for example, by affixing the label in a convenient location on the closure mechanism 842 as shown, or on the bag 841. The label, which may be printed as a simple adhesive label and affixed when the bag is initially filled with goods, includes a unique bar code assigned to the bag unit.

The slots 822 are shaped to correspond with the closure mechanism 841 provided on the bag unit 840 in a manner that ensures that bags are securely held when docked with the rail. In the illustrated embodiment, the closure mechanism 841 is shaped as a trapezoid, with the top edge longer than the bottom edge, with each of the slots 822 similarly shaped to receive and hold bags 840 by force of gravity. However, as noted above, many different types of bag closure mechanisms are known and could be adapted for use with an appropriately shaped rail.

Figure 21:
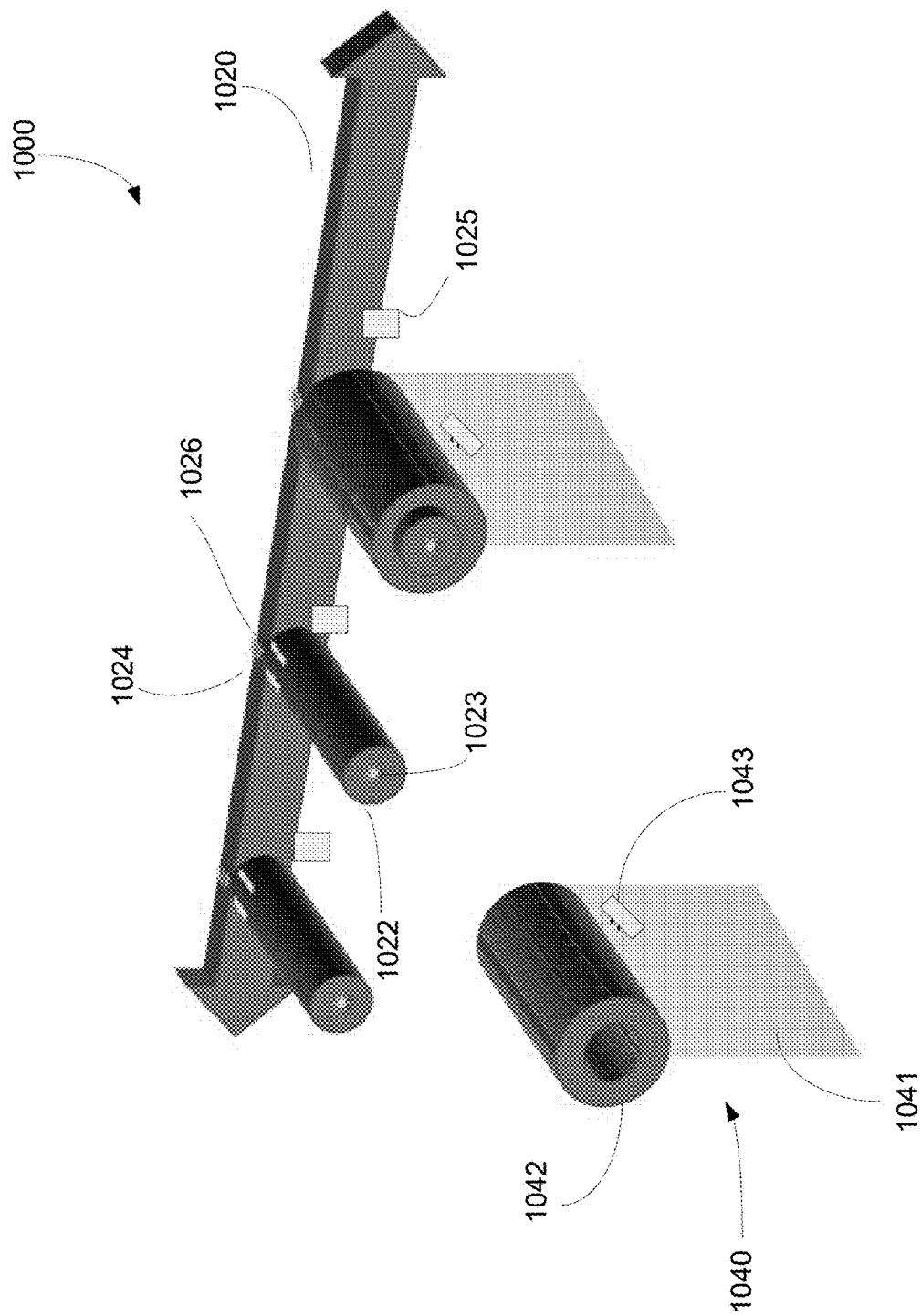
FIG. 21 is a schematic block diagram illustrating another alternative embodiment of a storage system.

Other suitable physical configurations could be implemented to provide the same features. For example, FIG. 21 shows an alternative embodiment of a storage system 1000 having a rail 1020, but rather than having locations adapted to receive the bags, the rail 102 includes a number of rigid posts 1022 extending from the rail, such that bag units could be placed onto the posts. In this example, the posts 1022 are cylindrical, with a first LED 1023 affixed at the distal end of each post and a second LED 1024 affixed on top of the rail above each post, with operation of the LEDs as status indicators as described above. Further, a sensor 1025 is affixed to the rail adjacent each post 1022 and configured to (1) detect that a bag unit has been hung on a post, and (2) identify the bag unit.

The bag unit 1040 includes a plastic bag 1041 and a closure mechanism 1042 integrated with the top of the bag. In this embodiment, the closure mechanism 1042 is an annular structure adapted to slide over the post 1022 and butt up to the rail. A label 1043 with a bar code is affixed to the bag 1041, or it could be affixed to the closure mechanism 1042. The location of the label on the bag or on the closure is important to specify so that the sensor 1025 is positioned appropriately to capture an image of the label for processing.

Optionally in this embodiment, a pair of thin sensors 1026 can be affixed at the proximal end of the post 1022, for example pressure sensors, and by the bag unit making physical contact with the sensors, bag placement is detected.

Figure 22A:
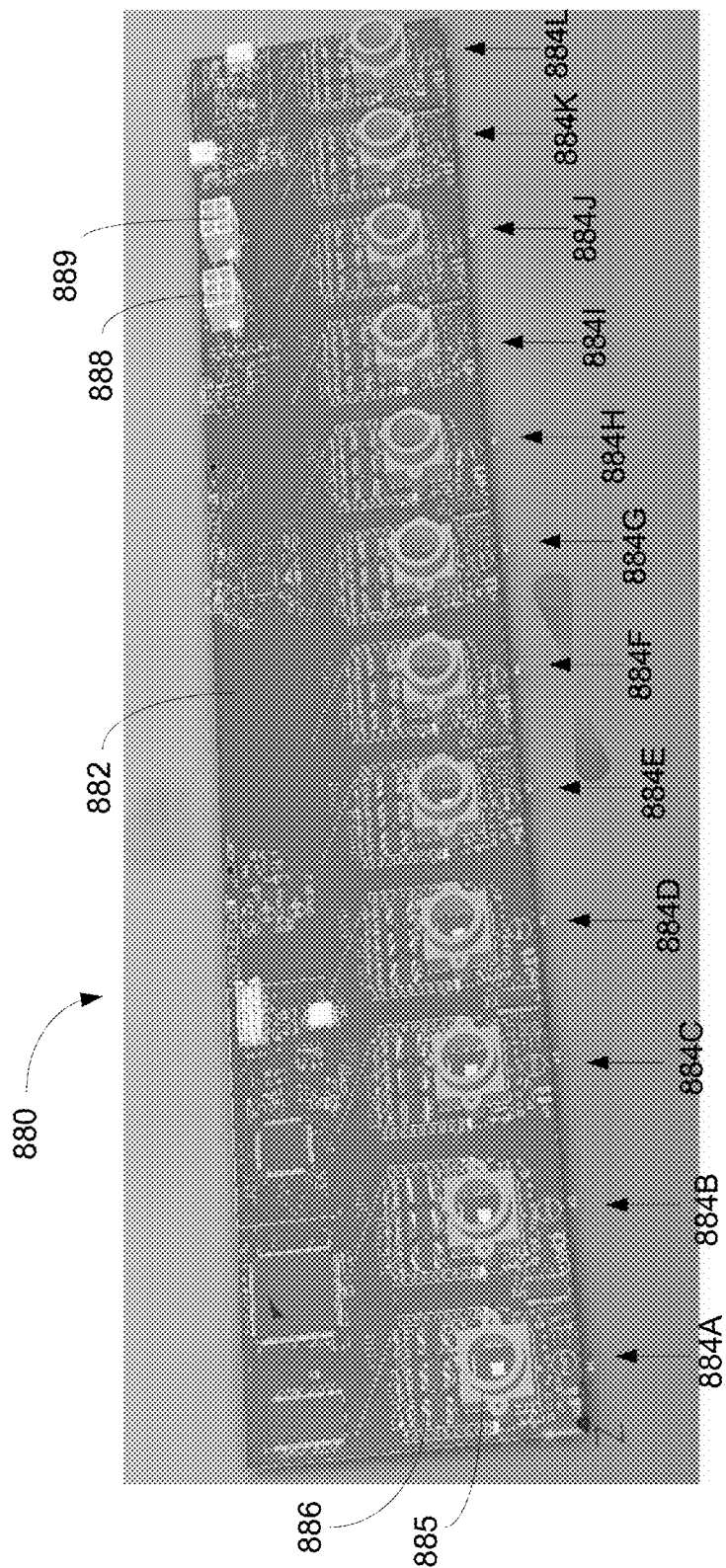
FIG. 22A is a front perspective view of a printed circuit board.
Figure 22B:
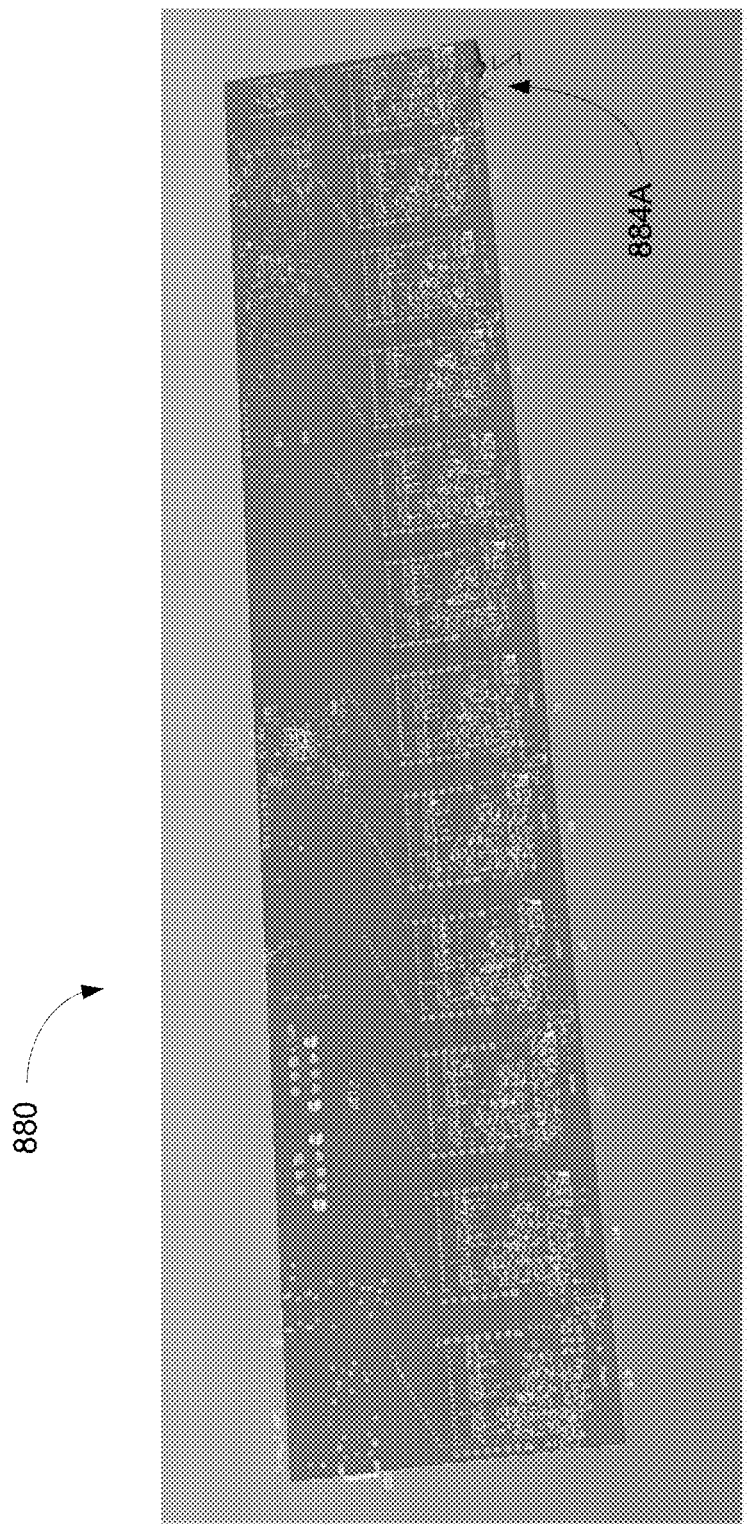
FIG. 22B is a rear perspective view of the printed circuit board.

One example of an electronic structure 880 is illustrated in FIGS. 22A (front or top) and 22B (rear or bottom). The electronic structure 880 is a circuit board 882 that is integrated within the physical structure 821 to form a rail or rail section, and may be built in virtually any length to accommodate a number of different locations for bag placement. In one example, the circuit board is four feet in length with sensors positioned along the length at one and one-half inches from each other. Each location has a corresponding mechanism for receiving a bag unit, e.g., as a receptacle (such as a slot) or as a post. In this example, twelve locations 884A-884L are configured on circuit board 882. Each location is configured virtually identically, except for a location identifier associated with each location. Thus, location 884A is assigned the first address for the circuit board 882, location 884B is assigned the second address for the circuit board, and so on. The circuit board 882 is assigned a unique rail ID upon installation and setup with the master controller.

With reference to location 884A, each location includes a sensor attachment 885 mounted onto a printed circuit 886, with imaging lens 887 affixed within the sensor attachment. and the printed circuit is coupled to a common bus for all the printed circuits on the circuit board. A local processor is coupled to the bus and configured to handle communication of signals to and from each printed circuit 886, and to and from the master controller. For example, a first connector 888 is provided for coupling with another rail before the current rail, and a second connector 889 is provided for coupling with another rail after the current rail, and thus a continuous bus is formed through all interconnected rail sections.

In one example of an operational process 1100, illustrated in FIG. 23, a bag unit 1040 having goods stored therein is placed over a post 1022 in step 1102. In step 1104, the sensor 1025 detects placement of the bag unit 1040 over the post 1022, and as a result of the detection, initiates a scan to obtain an image of the label 1042 affixed with the bag unit in step 1106.

In step 1108, the sensor stores the data to the local processor. The sensor data includes the location of the sensor, i.e., a digital address associated with the adjacent post, and the image of the label on the bag unit. In step 1110, the local processor adds the rail ID to the sensor data, and in step 1112 transmits a data packet to the master controller. In step 1114, the master controller translates the label image into a bag ID, and in step 1116, the master controller updates its record of inventory to reflect the newly added bag unit.

The status LEDs may be used during a bag placement in various ways. For example, the LEDs at a specific location may off when no bag is present at the location. However, when a bag is placed, the LEDs may blink to indicate that the system is processing the placement, and may resolve to a solid color when the bag has been recorded in inventory by the master controller.

An example process 1120 for retrieving goods is illustrated in FIG. 24. In step 1122, a request is received at the master controller to retrieve a specific order for delivery to a customer. In step 1124, the master controller determines the bag ID that was assigned to this particular customer's order when the bag was filled. In step 1126, using the bag ID, the master controller determines the location, i.e., the digital address of the bag (rail ID plus slot location), from its inventory record. In step 1128, the master controller sends a signal to the local processor to illuminate the LEDs at the specified location, and in step 1130, the local processor on the circuit board performs the action. In optional step 1132, the master controller generates a report and delivers the report to a user interface, e.g., an employee terminal or a customer kiosk, where the report identifies the customer order, and the specific location of the order in the product storage area.

Figure 25:
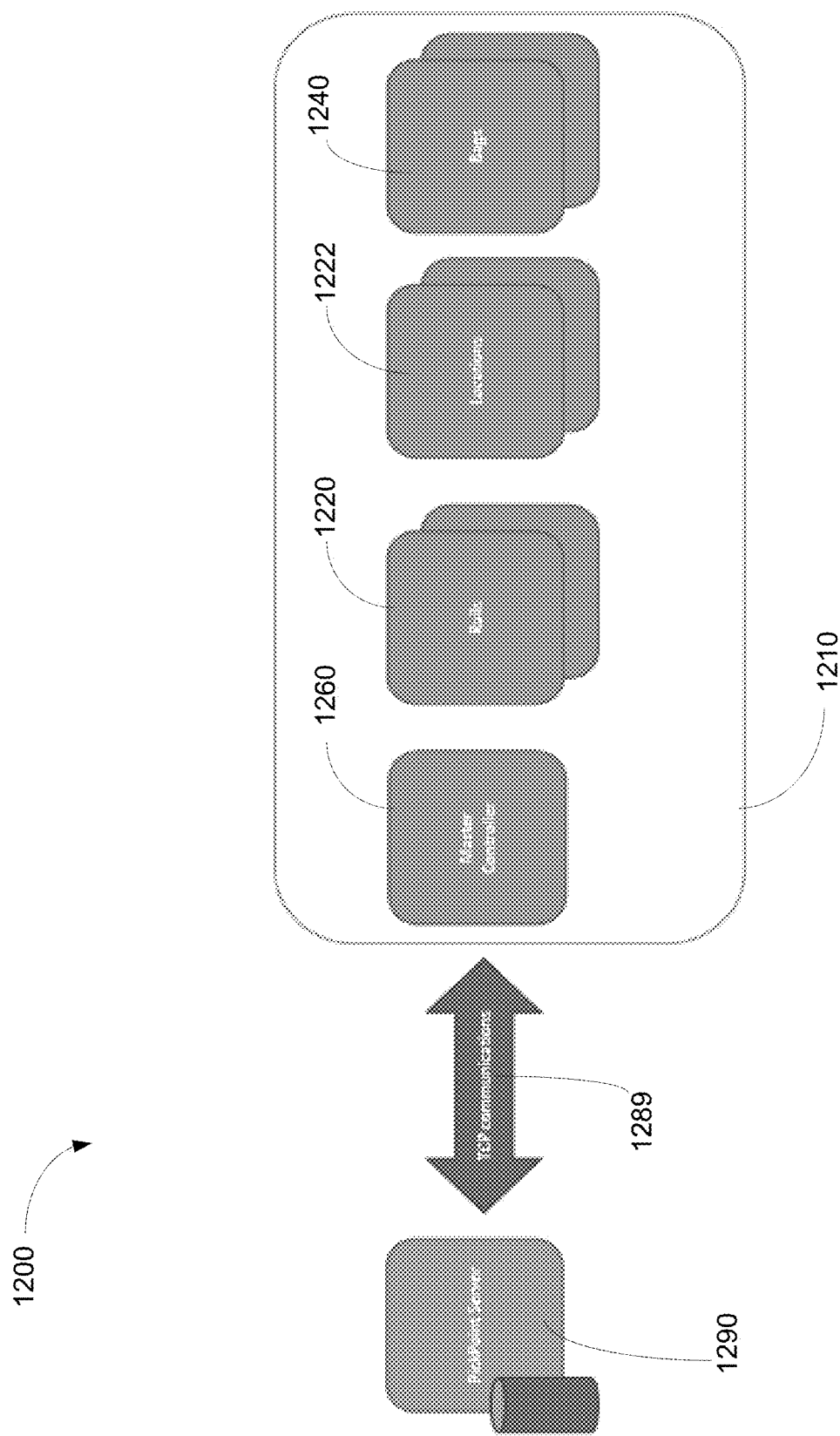
FIG. 25 is a schematic representation of one storage system.

Referring now to FIG. 25, one example of a storage system 1200 is illustrated. A server 1290 is configured to handle all input and output operations related to customer orders, for example, as a hosted end-user website. The server 1290 communicates with a local facility 1210 using conventional TCP communication protocols 1289. The local facility 1210 has its own master controller 1260 that manages the local system of rails 1220, locations 1222 in the rails, and bag units 1240 placed in locations on the rails, and manages communications between the master controller and the rails.

Figure 26:
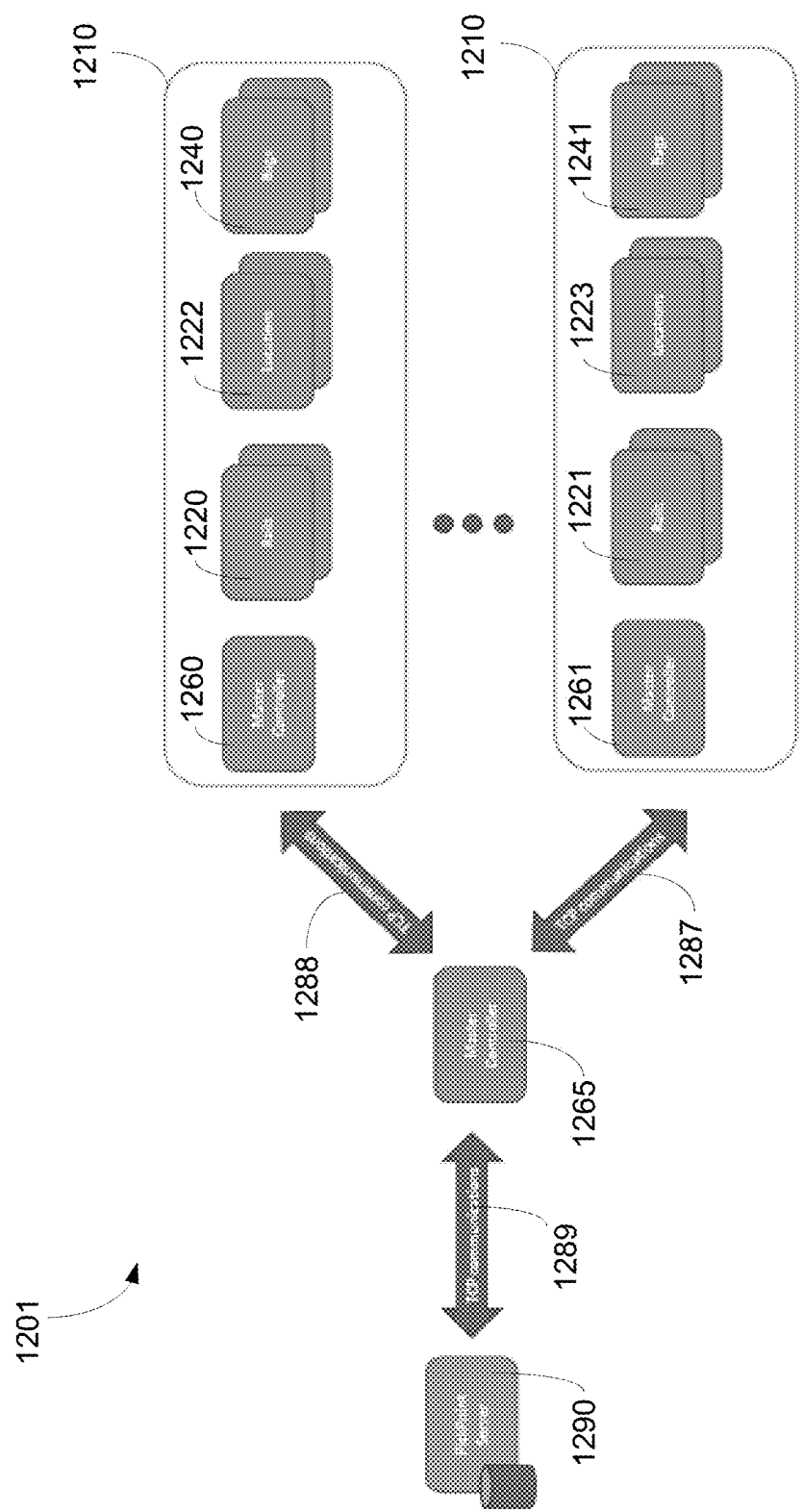
FIG. 26 is a schematic representation of another storage system.

A more complex system 1201 is illustrated in FIG. 26. In this example, the server 1290 is configured to communicates with multiple local facilities, such as local facility 1210 and local facility 1211, through a single global master controller 1265. The server 1290 communicates with the global master controller 1265 via TCP communication link 1289, and the global master controller communicates with facility 1210 via TCP communication link 1288 and with facility 1211 via TCP communication link 1287.

Local facility 1210 includes master controller 1260, rails 1220, locations 1222 in the rails, and bag units 1240 placed in locations on the rails, while local facility 1211 includes master controller 1261, rails 1221, locations 1223 in the rails, and bag units 1241 placed in locations on the rails.

The local master controller 860 is a computer-based device typically installed at a local storage facility in reasonable proximity to the rails of the storage system. The controller 860 may be specially constructed and configured for this application, or it may be a general-purpose computer having programmed instructions. The controller 860 should include adequate processing power to process and store signals and data for all attached rails and bags at the local storage facility, and should be configured to communicate in standard wired and/or wireless modes with the rails 820 at the local level. The controller 860 should also be configured to communicate with external resources as necessary. For example, multiple controllers each located at a different storage facility may each be configured to communicate with a centralized server via a network, e.g., the Internet, to facilitate central coordination and control of order control and delivery for a larger, regional or national storage and delivery system.

All connections and connectors provided should conform to existing standards and be readily available. The controller 860 should include physical buttons or switches to reset and cycle power. The harness for power and data should be properly rated for voltage/amperage not to exceed the Limited Power Source standards specified in IEC 60950-1.

Thus, the smart rail embodiments include all the circuitry and intelligence incorporated with the rail. Further, the smart rail includes either a receptacle configured to receive a similarly configured bag unit or its closure mechanism, or a post extending from the rail and configured to receive a similarly configured bag unit or its closure mechanism. The bag unit has a bag identifier affixed, which is scanned by a sensor adjacent a placement location when the bag unit is placed onto the rail. The rail circuitry then sends the bag identifier, the bag location, and the rail identifier to a controller for updating the inventory.

It will be understood that the inventive system has been described with reference to particular embodiments, however additions, deletions and changes could be made to these embodiments without departing from the scope of the inventive system. Although the order filling apparatus and method have been described include various components, it is well understood that these components and the described configuration can be modified and rearranged in various other configurations.

The invention claimed is:

1. An apparatus for product storage, comprising:
a rail having a length and a plurality of bag receiving locations defined along the length of the rail, each bag receiving location including a respective mechanism for receiving a bag unit;
an electronic structure integrated with the rail including a plurality of circuits, the electronic structure having a rail identifier, each circuit associated with a respective one of the plurality of bag receiving locations of the rail, and a plurality of sensors each coupled with each a respective circuit and affixed to the rail adjacent the respective bag receiving location;
each sensor is configured to detect placement of a bag unit onto the respective mechanism of the adjacent bag receiving location and to obtain a bag identifier for the bag unit; and
each circuit is configured to store the bag identifier and the corresponding bag receiving location for a placement of the bag unit, and then to transmit the bag identifier, the corresponding bag receiving location, and the rail identifier, to a controller for inventory management.

2. The apparatus of claim 1, further comprising:
the rail includes a plurality of sections each having a plurality of bag receiving locations defined along the section, each section having a unique rail identifier, and an electronic structure for each section.

3. The apparatus of claim 1, further comprising:
the mechanism is a receptacle adapted to receive a similarly configured bag unit.

4. The apparatus of claim 1, further comprising:
the mechanism is a post extending from the rail adapted to receive a similarly configured bag unit.

5. The apparatus of claim 1, further comprising:
the sensor is configured to scan the bag unit to obtain the bag identifier.

6. The apparatus of claim 1, further comprising:
each bag receiving location of the rail is assigned a digital address.

7. The apparatus of claim 1, further comprising:
each bag receiving location having an indicator lamp that is illuminated to indicate status of the respective bag receiving location.

8. A system, comprising:
a plurality of rails, each rail having a length and a plurality of bag receiving locations defined along the length of the rail, each bag receiving location including a respective mechanism for receiving a bag unit;
a plurality of electronic structures, each electronic structure integrated with a respective rail and including a plurality of circuits, each electronic structure having a rail identifier, each circuit associated with a respective one of the plurality of bag receiving locations of the respective rail, and a sensor coupled with each respective circuit and affixed to the respective rail adjacent the respective bag receiving location;
each sensor is configured to detect placement of a bag unit onto the mechanism of the adjacent bag receiving location and to obtain a bag identifier for the bag unit; and
each circuit is configured to store the bag identifier and the corresponding bag receiving location for a placement of the bag unit, and then to transmit the bag identifier, the corresponding bag receiving location, and the rail identifier, to a controller for inventory management.

* * * * *